United States Patent
Badylak et al.

(10) Patent No.: US 9,814,744 B2
(45) Date of Patent: Nov. 14, 2017

(54) DECELLULARIZED ADIPOSE CELL GROWTH SCAFFOLD

(75) Inventors: Stephen F. Badylak, Pittsburgh, PA (US); Bryan N. Brown, Pittsburgh, PA (US); John M. Freund, Pittsburgh, PA (US); J. Peter Rubin, Pittsburgh, PA (US)

(73) Assignee: University of Pittsburg—Of the Commonwealth System of Higher Education, Pittsburgh, PA (US)

( * ) Notice: Subject to any disclaimer, the term of this patent is extended or adjusted under 35 U.S.C. 154(b) by 115 days.

(21) Appl. No.: 13/515,661

(22) PCT Filed: Dec. 20, 2010

(86) PCT No.: PCT/US2010/061218
§ 371 (c)(1),
(2), (4) Date: Jan. 10, 2013

(87) PCT Pub. No.: WO2011/087743
PCT Pub. Date: Jul. 21, 2011

(65) Prior Publication Data
US 2013/0202563 A1    Aug. 8, 2013

Related U.S. Application Data

(60) Provisional application No. 61/289,082, filed on Dec. 22, 2009.

(51) Int. Cl.
| | | |
|---|---|---|
| *A01N 63/00* | (2006.01) |
| *A01N 65/00* | (2009.01) |
| *A01N 1/00* | (2006.01) |
| *A01N 1/02* | (2006.01) |
| *A61K 35/35* | (2015.01) |
| *A61L 26/00* | (2006.01) |
| *A61L 27/38* | (2006.01) |
| *A61L 27/60* | (2006.01) |
| *C07K 14/78* | (2006.01) |
| *C12N 5/00* | (2006.01) |
| *C12N 5/0775* | (2010.01) |

(52) U.S. Cl.
CPC .......... *A61K 35/35* (2013.01); *A61L 26/0057* (2013.01); *A61L 26/0076* (2013.01); *A61L 27/3804* (2013.01); *A61L 27/60* (2013.01); *C07K 14/78* (2013.01); *C12N 5/0068* (2013.01); *C12N 5/0667* (2013.01); *C12N 2533/90* (2013.01)

(58) Field of Classification Search
None
See application file for complete search history.

(56) References Cited

U.S. PATENT DOCUMENTS

| | | |
|---|---|---|
| 4,782,025 A | 11/1988 | Inoue et al. |
| 4,902,508 A | 2/1990 | Badylak et al. |
| 4,956,178 A | 9/1990 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,777,231 B1 | 8/2004 | Katz et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 8,361,503 B2 | 1/2013 | Badylak et al. |
| 2003/0036797 A1* | 2/2003 | Malaviya et al. ......... 623/14.12 |
| 2003/0036801 A1* | 2/2003 | Schwartz et al. ......... 623/23.63 |
| 2005/0013870 A1* | 1/2005 | Freyman et al. ............ 424/520 |
| 2005/0215803 A1* | 9/2005 | Abril ...................... C07F 9/103 554/78 |
| 2008/0069852 A1* | 3/2008 | Shimp et al. ................. 424/423 |
| 2008/0260831 A1 | 10/2008 | Badylak et al. |

(Continued)

FOREIGN PATENT DOCUMENTS

| | | |
|---|---|---|
| WO | 2008146956 A1 | 12/2008 |
| WO | 2011072393 A1 | 6/2011 |
| WO | 2013009595 A2 | 1/2013 |

OTHER PUBLICATIONS

Ferraz et al., J. Biochem. Biophys. Methods, 58:187-193 (2004).*

(Continued)

*Primary Examiner* — Thomas J Visone

(74) *Attorney, Agent, or Firm* — The Webb Law Firm

(57) ABSTRACT

Provided herein are methods of making a cell growth scaffold from adipose tissue, cell growth scaffolds having low lipid content and methods of using the cell growth scaffold.

9 Claims, 13 Drawing Sheets

(56) References Cited

U.S. PATENT DOCUMENTS

2009/0163990 A1* 6/2009 Yang et al. ............. 623/1.15
2011/0151011 A1* 6/2011 Flynn ..................... 424/490

OTHER PUBLICATIONS

Flynn et al., Biomater., 28:3834-3842 (2007).*
Lasner et al., Arch. Biochem. Biophys., 317(2):391-396 (1995).*
Ly et al., Biophys. J. 87:1013-1033 (2004).*
Amatschek et al., Blood and lymphatic endothelial cell-specific differentiation programs are stringently controlled by the tissue environment, Blood, Jun. 1, 2007, 4777-4785, vol. 109, No. 11.
Badylak et al. Esophageal reconstruction with ECM and muscle tissue in a dog model, J Surg Res, 2005, 87-97, 128.
Badylak et al. Extracellular matrix as a biological scaffold material: Structure and function, Acta Biomater, 2009, 1-13, 5.
Baker et al., Mass spectral imaging of glycophospholipids, cholesterol, and glycophorin A in model cell membranes, Langmuir., Oct. 21, 2008, 11803-11810, 24(20).
Bissell et al., Dynamic reciprocity: how do extracellular matrix and hormones direct gene expression?, Mechanisms of Signal Transduction by Hormones and Growth Factors, 1987, Alan R. Liss, Inc., pp. 251-262.
Brown et al., Surface characterization of extracellular matrix scaffolds, Biomaterials, Jan. 2010, 428-437, 31(3).
Brown et al., The basement membrane component of biologic scaffolds derived from extracellular matrix, Tissue Eng., 2006, 519-526, vol. 12, No. 3.
Brown et al., Macrophage phenotype and remodeling outcomes in response to biologic scaffolds with and without a cellular component, Biomaterials, Mar. 2009, 1482-1491, 30(8).
Canavan et al., Comparison of native extracellular matrix with adsorbed protein films using secondary ion mass spectrometry, Langmuir., 2007, 50-56, 23.
Cheng et al., Chondrogenic differentiation of adipose-derived adult stem cells by a porous scaffold derived from native articular cartilage extracellular matrix, Tissue Eng. Part A, 2009, 231-241, 15(2).
Choi et al., Human extracellular matrix (ECM) powders for injectable cell delivery and adipose tissue engineering, J. Controlled Release, 2009, 2-7, 139.
Choi et al., Fabrication of porous extracellular matrix scaffolds from human adipose tissue, Tissue Eng. Part C, 2010, 387-396, 16(3).
Gilbert et al., Quantification of DNA in biologic scaffold materials, J Surg Res., Mar. 2009, 135-139, 152(1).
Gilbert et al., Decellulariztion of tissues and organs, Biomaterials, 2006, 3675-3683, 27.
Heydarkhan-Hagvall et al., Three-dimensional electrospun ECM-based hybrid scaffolds for cardiovascular tissue engineering, Biomaterials, Jul. 2008, 2907-2914, 29(19).
Huber et al., Extracellular matrix as a scaffold for laryngeal reconstruction, Ann Otol Rhinol Laryngol, 2003, 428-433, 112.
Le Roux, Endoscopic urethroplasty with unseeded small intestinal submucosa collagen matrix grafts: a pilot study, J Urol., Jan. 2005, 140-143, 173.
Magnusson et al., Application of multivariate analysis of ToF-SIMS Spectra for studying the effect of high glucose intake on aortic lipid profile, Applied Surface Science, 2008, 6580-6585, 254.
Mantovani et al., Reconstructive urethroplasty using porcine acellular matrix, European Urology, 2003, 600-602, 44.
McQuaw et al., Lateral heterogeneity of dipalmitoylphosphatidylethanolamine-cholesterol Langmuir-Blodgett films investigated with imaging time-of-flight secondary ion mass spectrometry and atomic force microscopy, Langmuir, 2005, 807-813, 21.
McQuaw et al., Localization of sphingomyelin in cholesterol domains by imaging mass spectrometry, Langmuir, May 8, 2007, 5645-5650, 23(10).
Sclamberg et al., Six-month magnetic resonance imaging follow-up of large and massive rotator cuff repairs reinforced with porcine small intestinal submucosa, J Shoulder Elbow Surg., 2004, 538-541, 13.
Sellaro et al., Maintenance of human hepatocyte function in vitro by liver-derived extracellular matrix gels, Tissue Eng Part A, 2010, 1075-1082, 16(3).
Sellaro et al.. Maintenance of hepatic sinusoidal endothelial cell phenotype in vitro using organ-specific extracellular matrix scaffolds, Tissue Eng., 2007, 2301-2310, 13(9).
van Amerongen et al., The enzymatic degradation of scaffolds and their replacement by vascularized extracellular matrix in the murine myocardium, Biomaterials, 2006, 2247-2257, 27.
Wagner et al., Characterization of adsorbed protein films by time-of-flight secondary ion mass spectrometry with principal component analysis, Langmuir, 2001, 4649-4660, 17.

* cited by examiner

DECELLULARIZED ADIPOSE CELL GROWTH SCAFFOLD

CROSS REFERENCE TO RELATED APPLICATIONS

This application is a National Stage of International Patent Application No. PCT/US2010/061218, filed Dec. 20, 2010, which claims the benefit under 35 U.S.C. §119(e) of U.S. Provisional Patent Application No. 61/289,082, filed Dec. 22, 2009, each of which is herein incorporated by reference in its entirety.

STATEMENT REGARDING FEDERALLY SPONSORED RESEARCH OR DEVELOPMENT

This invention was made with government support under Grant Nos. CA114246 and AR054940 awarded by the National Institutes of Health. The government has certain rights in the invention.

Biologic scaffolds composed of extracellular matrix (ECM) are utilized in numerous regenerative medicine applications to facilitate the constructive remodeling of tissues and organs. The mechanisms by which the host remodeling response occurs are not fully understood, but recent studies suggest that both constituent growth factors and biologically active degradation products derived from ECM play important roles.

There are a number of surgical options for the repair of adipose tissue following trauma or resection. These options generally include the use of autologous tissue transplantation (1, 2). While these methods are generally sufficient for tissue repair, there are a number of limitations regarding the long-term survival and functionality of the transplanted tissue. These include both donor and recipient site morbidity, with many adipose tissue transplants experiencing volume reduction and necrosis due to disruption of the vascular supply (3). Methods that maintain the vascular supply during transplant are available. However, tissues transplanted using these methods are also subject to significant morbidity (3). A number of synthetic and biologically derived materials have been utilized as injectable tissue fillers and as volume filling constructs for soft tissue repair (4, 5). However, these materials are often subject either to resorption and subsequent loss of volume and mechanical integrity or to a foreign body response which leads to an undesirable outcome due to chronic inflammation and encapsulation. Therefore, an off-the-shelf scaffold material which is capable of effectively supporting the growth, differentiation, and transplantation of adipose tissue specific cells without evoking a significant foreign body response is of great interest in the fields of plastic and reconstructive surgery.

The extracellular matrix (ECM) represents the secreted product of resident cells within every tissue and organ and thus defines a preferred collection of structural and functional molecules best suited to support the viability and phenotype of those cells. The ECM is in a state of dynamic reciprocity with the cells of each tissue (Bissell, M. J., and Aggeler, J. Dynamic reciprocity: how do extracellular matrix and hormones direct gene expression? Prog Clin Biol Res 249, 251, 1987 and Amatschek, S., et al. Blood and lymphatic endothelial cell specific differentiation programs are stringently controlled by the tissue environment. Blood 109(11), 4777, 2007), and the growth factors, cytokines, chemokines, and other signaling molecules within the ECM play important roles in development, homeostasis, and response to injury. A variety of mammalian tissues and organs, including the small intestine, liver, urinary bladder, arterial vasculature, heart valves, and dermis, have been decellularized, and the remaining ECM used as a biologic scaffold to support the reconstruction of injured or missing tissues (Sclamberg, S. G., et al. Six-month magnetic resonance imaging follow-up of large and massive rotator cuff repairs reinforced with porcine small intestinal submucosa. J Shoulder Elbow Surg 13(5), 538, 2004; Le Roux, P. J. Endoscopic urethroplasty with unseeded small intestinal submucosa collagen matrix grafts: a pilot study. J Urol 173(1), 140, 2005; Mantovani, F., et al. Reconstructive urethroplasty using porcine acellular matrix. Eur Urol 44(5), 600, 2003; van Amerongen, M. J., et al. The enzymatic degradation of scaffolds and their replacement by vascularized extracellular matrix in the murine myocardium. Biomaterials 27(10), 2247, 2006; Badylak, S. F., et al. Esophageal reconstruction with ECM and muscle tissue in a dog model. J Surg Res 128(1), 87, 2005; and Huber, J. E., et al. Extracellular matrix as a scaffold for laryngeal reconstruction. Ann Otol Rhinol Laryngol 112(5), 428, 2003). The mechanisms by which these biologic scaffolds facilitate tissue remodeling include both contact guidance and molecular signaling, but the temporal and spatial patterns of these events remain largely unknown.

Previous studies have shown that nonphysiologic methods of ECM degradation such as acid and heat can produce low molecular weight molecules that have angiogenic, chemoattractant, and antimicrobial properties. Interestingly, degradation of the ECM scaffold is necessary to realize these biologic effects. It has been clearly shown that intact ECM has no antimicrobial effects, while degradation products of the same ECM are able to strongly inhibit bacterial growth. Similarly, if ECM scaffolds are chemically crosslinked such that they are resistant to degradation, the host remodeling response is markedly altered toward fibrous encapsulation and chronic inflammation rather than constructive remodeling. It is clear that the products and biologic effects of ECM degradation are different from the components of the intact ECM.

The extracellular matrix (ECM) of each tissue and organ consists of the secreted products of its resident cell population. In turn, the phenotype and behavior of the resident cells is affected by signaling through the ECM, resulting in a state of dynamic reciprocity with the matrix. Thus, the ECM logically represents an appropriate substrate for the support of tissue specific cell phenotype and function. Biologic scaffold materials composed of mammalian extracellular matrix (ECM) have been harvested from a wide variety of tissues and organs, and recent work suggests that ECM scaffold materials harvested from different tissues each possess a distinct composition and ultrastructure. However, it is unknown whether the tissue-specific composition and architecture of ECM scaffolds derived from individual organs are necessary to maintain the phenotype and three-dimensional arrangement of cells native to those same tissues when compared to ECM materials derived from non-homologous sources (Sellaro T L, et al. Maintenance of human hepatocyte function in vitro by liver-derived extracellular matrix gels. Tissue Eng Part A. 16:1075-82 and Sellaro T L, et al. Maintenance of hepatic sinusoidal endothelial cell phenotype in vitro using organ-specific extracellular matrix scaffolds. Tissue Eng. 13:2301-10. 2007). Adipose tissue represents a potentially abundant source of ECM and may also represent an ideal scaffold material for the growth, differentiation, and phenotypic maintenance of cells that have been harvested from adipose tissue. However, the methods by which adipose tissue ECM scaffolds are produced may have distinct effects upon the structural and functional components of the resultant scaffold material and the subsequent ability of the material to function in in vivo tissue engineering and regenerative medicine applications.

In general, the methods used to decellularize and isolate ECM include a combination of physical (freezing, pressure, sonication, agitation) and chemical (enzyme, detergent, acid, alkaline) treatments which are typically tailored to the tissue or organ of interest. Logically, each of these treatments affects the components which are retained within the extracellular matrix and may alter the mechanical and material properties, ultrastructure, ability to support growth and differentiation of cells in vitro, and the host response following implantation.

When tissues have been efficiently decellularized, the ECM specific structural and functional components which remain (i.e. collagen, laminin, fibronectin, growth factors, etc.) are relatively well conserved across mammalian species and, therefore, do not evoke adverse immune reaction. However, a number of recent studies have shown that cellular components may remain following decellularization in a number of ECM materials, even those which have received FDA approval for clinical use. Further studies have suggested that inefficient removal of cellular contents such as DNA and the α-gal epitope during decellularization may be responsible for inflammation and poor outcomes following implantation. However, when present in sufficiently small quantities, neither DNA nor the α-gal epitope have been associated with poor outcomes in vivo.

Adipose tissue is widely available from both animal and human sources. Although widely available, efficient, effective and commercially practicable processing methods are not. As such, a simple, inexpensive method of producing decellularized cell growth scaffolds from adipose tissue is most desirable.

SUMMARY

Described herein are methods of making a cell growth scaffold from adipose tissue. A limitation of previous methods of producing ECM products from adipose tissue is residual lipophilic constituents, e.g., lipids, fats, oils, grease, etc. remaining in the matrix after preparation. The methods described herein produce an ECM product with little or no remaining lipophilic constituents. The method comprises removing lipophilic constituents from a decellularized cell growth scaffold prepared from adipose tissue.

DETAILED DESCRIPTION

Figure 1:
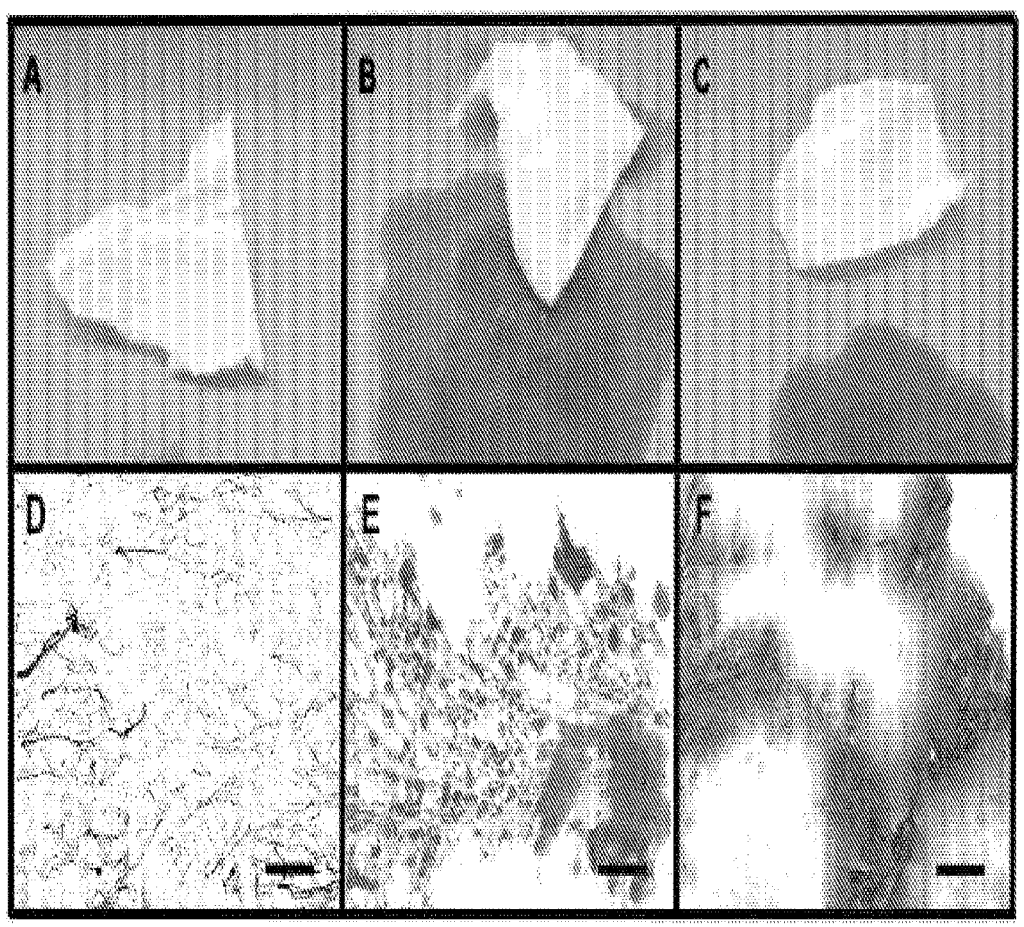
FIG. 1. Gross morphology (A-C) and oil red O staining (D-F, 10× magnification) of materials resulting from Method A (A, D), Method B (B, E), and Method C (C, F). Red staining is indicative of lipid content. Scale bar=200 µm.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

By "biocompatible," it is meant that a polymer composition and its normal degradation in vivo products are cytocompatible and are substantially non-toxic and non-carcinogenic in a patient within useful, practical and/or acceptable tolerances. By "cytocompatible," it is meant that the polymer can sustain the viability and growth of a population of cells and/or the polymer composition, device, and degradation products, thereof are not cytotoxic and/or carcinogenic within useful, practical and/or acceptable tolerances. For example, the polymer when placed in a human epithelial cell culture does not adversely affect the viability, growth, adhesion, and number of cells. In one non-limiting embodiment, the compositions, and/or devices are "biocompatible" to the extent they are acceptable for use in a human or veterinary patient, for example, according to applicable regulatory standards in a given jurisdiction. In another example the biocompatible polymer, when implanted in a patient, causes little or no adverse reaction or substantial harm to cells and tissues in the body, or, alternately, does not cause a substantial adverse reaction or substantial harm to cells and tissues in the body, for instance, the polymer composition or device does not cause necrosis or an infection resulting in harm to tissues from the implanted scaffold.

A progenitor cell is a cell that can differentiate under certain conditions into a more-differentiated cell type. Non-limiting examples of progenitor cells include stem cells that may be totipotent, pluripotent, multipotent stem cells, or referred to as progenitor cells. Additional non-limiting examples of progenitor cells include perivascular stem cells, blastema cells, and multilineage progenitor cells.

As used herein, the "treatment" or "treating" of a wound or defect means administration to a patient by any suitable dosage regimen and administration route of a composition with the object of achieving a desirable clinical/medical end-point, including attracting progenitor cells, healing a wound, correcting a defect, etc.

As used herein, the term "patient" refers to members of the animal kingdom including but not limited to mammals and human beings and is not limited to humans or animals in a doctor-patient or veterinarian-patient relationship.

The cell growth scaffolds (matrices) described herein are useful for growing cells, tissues, organs in virtually any in vivo, ex vivo, or in vitro use. The material can be used as a substrate to facilitate the growth and differentiation of cells, whether in vivo or in vitro, into tissue, organ or body part precursors (e.g., anlagen), or even mature tissues or structures. The materials are useful in vitro as a cell growth medium to support the growth in culture of adipose cells, adipose cell precursor cells, such as adipose-derived stem cells, or virtually any other type of cells or cell-lines, including stem cells, progenitor cells or differentiated cells. The materials are expected to be useful in vivo as a cell growth scaffold for tissue growth for any useful purpose, including repair, replacement or augmentation of tissue in a patient in either humans or animals. For example, the materials are expected to be useful in repair and/or replacement of tissue lost or damaged during trauma or surgery, for example in loss of tissue after tumor removal. The materials are expected to be useful for cosmetic purposes, for example in breast, lip or buttock augmentation. The materials described herein can be molded or contained within a structure to form desired shapes, such as, for cartilage repair or replacement by seeding the material with, e.g., chondrocytes and/or chondroprogenitor cells.

The cell growth scaffold described herein may be prepared by many methods. Tissue for preparation of ECM can be harvested in a large variety of ways and once harvested, a variety of portions of the harvested tissue may be used. Adipose tissue may be harvested from any suitable animal species, and typically mammalian species donor, living or deceased. For example, adipose tissue from pigs and cattle can be readily obtained from a slaughterhouse or abbatoir. Human adipose tissue can be obtained, for example, by liposuction. Irrespective of source, adipose tissue from one species is expected to be substantially equally useful in other species (e.g., pig adipose tissue in humans), as is indicated in Example 1, below, and as established in the relevant field by the demonstrated utility of materials such as pig intestine and urinary bladder as sources of ECM-derived scaffolds for use in growth of human cells and tissue. Nevertheless, in certain situations, use of same-species adipose tissue may be favored if one or more characteristics of the same-species tissue is required or preferable, such as the presence of human-specific ECM structures or matricrypric peptides.

Once harvested, it may be preferable in many instances to freeze the tissue. After thawing, it also may be desirable to massage and/or comminute the tissue by any useful method, including by, crushing, pulverizing, rolling, squeezing, sonicating, slicing, chopping, grinding, homogenizing, etc., so long as the massaging and/or comminuting step does not break down the matrix within the tissue to prevent its use as a cell growth matrix. This may be accomplished by hand, or by use of suitable machinery, comprising, for example and without limitation, cutter(s), roller(s), press(es), chopper(s), etc. Reasons for massaging the adipose tissue include to break up the cells within the tissue to the extent is can be processed more efficiently in later steps and/or to initially crush or lyse cells present in the sample. While these steps are not necessary in many instances, they may be preferred where the adipose tissue is provided/available in large pieces and/or contains sinewy materials.

Next, the tissue is treated with a protease, optionally in the presence of a chelating agent, such as EDTA or EGTA. In one embodiment, the protease is trypsin, though many examples of other proteases exist, such as pepsin, trypsin, and papain. After digestion, the material is washed, e.g., in water or PBS, and may be massaged and/or comminuted as described above.

After protease digestion, the material is washed, preferably with shaking (agitation, etc.) with a surfactant, preferably a gentle, non-ionic and/or non-denaturing surfactant.

Exemplary surfactants include: Triton X-100, NP-40, etc. The sample then can be washed with water, or other aqueous solvent, such as PBS, saline, etc. and is then washed with an emulsifier, such as deoxycholic acid, lecithin, etc., typically shaking. An emulsifier is any substance capable of forming an oil in water emulsion or micellular structures comprising oil and water. The sample again is washed.

In most instances, it is preferable to disinfect the sample, which can be accomplished by any useful method, including by chemical disinfection (e.g., with ethanol) or by irradiating the sample (e.g., with gamma-irradiation). It also is preferable to depyrogenate the sample, by washing with a compound useful for such purposes, such as peracetic acid.

At that point, one undesirable element present in the sample is lipids (including fats and/or grease). A major portion of the lipids can be removed by blotting with a suitably absorbant material, such as tissue paper, filter paper, aluminum oxide or talc. While blotting is effective to some extent in removing lipids, in some instances, substantial lipids remain. Further, blotting is a wasteful, costly and time-consuming process that does not as thoroughly contact all portions of the sample as well as a solvent would. As such, the sample can be washed with propanol, e.g., n-propanol (1-propanol), isopropanol (2-propanol) or mixtures thereof. The sample may be agitated while washing in a propanol, and multiple washes may be used. Once the sample has been washed with a propanol it is washed in water, saline (e.g., normal saline, PBS (phosphate-buffered saline), cell growth media, or any other suitable composition typically comprising water and one or more salt, buffer, chelating agent, etc. It then can be lyophilized for storage, or used in its "wet" state.

Propanol refers to a mono-OH-substituted propane, so it is either n-propanol or isopropanol.

In the methods described herein, choice and ranges for the various constituents, such as the protease(s), surfactant and emulsifier are not provided. Applicants have provided examples of each and with experimentation well within the abilities of those of ordinary skill in the relevant art(s), those persons can easily determine and optimize other concentrations of the listed constituents, or equivalents thereof, without undue experimentation.

At this point, the scaffold may be considered as ready for use. It can be packaged, distributed or used in at this point. In one embodiment, the scaffold is used as-is. It may be the case that fine particles are not necessary for the end-use of the scaffold. In such a case, the scaffold can be used for bulk applications, such as a filler in a breast implant or other fairly large structure. In another embodiment, the scaffold is comminuted into small grains or a powder. This fine material may be used for a multitude of purposes. The fine particles can be hydrated in water, saline or a suitable buffer or medium to produce a gel that can be injected into a patient at a desirable site, such as in a wound. In one instance, the gel can be injected in a bone breakage or in a hole drilled in bone to facilitate repair and/or adhesion of structures, such as replacement ligaments, to the bone. In another use, finely comminuted particles can be sprayed onto a surface of a patient, such as in the case of large surface abrasions or burns. The scaffold can also be sprayed onto skin sutures to inhibit scarring. The finely comminuted particles may have a maximum size of 250 µM (microns or micrometers) or less.

Although numerous methods exist, two exemplary methods may be used to produce a particulate form of the scaffold. The first method involved lyophilizing the disinfected material and then immersing the sample in liquid nitrogen. The snap frozen material is then reduced to small pieces with a blender so that the particles are small enough to be placed in a rotary knife mill, such as a Wiley mill. A #60 screen can be used to restrict the collected powder size to less than 250 mm. A Sonic sifter or other classification device can be used to remove larger particles and/or to obtain a particle size distribution within a desired range. A second method is similar to the previous method except the sample is first soaked in a 30% (w/v) NaCl solution for 5 min. The material is then snap frozen in liquid nitrogen to precipitate salt crystals, and lyophilized to remove residual water. This material is then comminuted as described in above. By precipitating NaCl within the sample, it is expected that the embedded salt crystals would cause the material to fracture into more uniformly sized particles. The particles are then suspended in deionized water and centrifuged for 5 min at 1000 rpm three times to remove the NaCl. The suspension is snap frozen and lyophilized again. Finally, the powder is placed in a rotary knife mill to disaggregate the individual particles.

The scaffolding can be placed inside a "bag" of, for example, a biodegradable cell-growth scaffold or ECM-derived material, such as urinary bladder-derived or intestine-derived ECM material to produce a larger three-dimensional structure, such as an orthopedic implant for cartilage repair (e.g., knee or TMJ cartilage repair) or an implant for breast reconstruction or augmentation. In such a case, a bag or cover of a desirable size and shape is formed from sheets of ECM material or other biocompatible and preferably biodegradable polymeric material, and then the bag or cover can be filled with the adipose tissue-derived scaffold described herein. The shape of the device or implant can vary with its intended use. Non-limiting example of the shape of the device may be spheriodal, which may be oblate, spherical or prolate, or disk-shaped. In use as a breast implant, the device may be an oblate (flattened) spheroid. It may be preferable to manufacture and even distribute the cover structure filled with the adipose-derived material described herein in its dry form and later hydrate the structure in a suitable aqueous solution. The cover may be molded into a useful shape by any useful molding technique, such as the shape of cartilage for the ear, nose, knee, TMJ, rib, etc., prior to filling the molded cover with the scaffold material described herein. In one example, a biodegradeable polymeric matrix (e.g., PEUU or PEEUU) is sprayed or electrodeposited onto a mold. The resultant molded cover can then be filled with the adipose-derived material. Heat, for example, may be used to seal the cover.

Commercially available ECM preparations, especially those in sheet form, can be used to shape the structures described herein, such as the "bag" described above. In one non-limiting embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another non-limiting embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

Prior to implantation, the scaffold may be placed in a suitable tissue culture container with suitable medium and cells can be placed in contact with the matrix. The cells can be cultured for any suitable time period and then implanted in a patient. The matrix also can be dispersed in an aqueous solvent, such as water, saline (e.g., 0.9% saline) or PBS and painted, sprayed or otherwise distributed on or in a wound of a patient to facilitate wound healing.

Prior to implantation or other uses of the scaffold described herein, cells or other compositions, such as drugs or cytokines may be dispersed into the scaffold.

Virtually any cell type can be dispersed into the scaffold. The cells may be stem cells, progenitor cells, differentiated cells, cell cultures etc. The cells may be xenogeneic, allogeneic, isogeneic (autologous) in origin. The cells can be genetically modified, for example, to produce a desirable cytokine or chemoattractant.

U.S. Pat. No. 6,777,231, incorporated herein by reference for its technical disclosure, describes various lipo-derived stem cells, and briefly described a method of making a lipo-derived matrix for growth of cells. Methods of making cells useful in the methods and compositions described herein are described in that reference, as well as methods of modifying cells for use in the methods and compositions described herein.

In one embodiment, adipose stem cells are propagated in the cell growth scaffolds described herein. Adipose stem cells are of mesodermal origin. They typically are pluripotent, and have the capacity to develop into mesodermal tissues, such as: mature adipose tissue; bone; heart, including, without limitation, pericardium, epicardium, epimyocardium, myocardium, pericardium, and valve tissue; dermal connective tissue; hemangial tissues; muscle tissues; urogenital tissues; pleural and peritoneal tissues; viscera; mesodermal glandular tissues; and stromal tissues. The cells not only can differentiate into mature (fully differentiated) cells, they also can differentiate into an appropriate precursor cell (for example and without limitation, preadipocytes, premyocytes, preosteocytes). Also, depending on the culture conditions, the cells can also exhibit developmental phenotypes such as embryonic, fetal, hematopoetic, neurogenic, or neuralgiagenic developmental phenotypes.

In one embodiment, a patient's own cells are dispersed within the matrix. For example, in the production of cartilaginous tissue, chondrocytes and/or chondroprogenitor cells can be dispersed within the matrix and optionally grown ex vivo prior to implantation. Likewise, skin cells of a patient can be dispersed within the scaffolding prior to implantation on a damaged skin surface of a patient, such as a burn or abrasion.

In another embodiment, at least one therapeutic agent is added to the scaffold described herein before it is implanted in the patient or otherwise administered to the patient. Generally, the therapeutic agents include any substance that can be coated on, embedded into, absorbed into, adsorbed to, or otherwise attached to or incorporated onto or into the cell growth scaffold or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a cell growth scaffold comprising neurotrophic agents or cells that express neurotrophic agents may be applied to a wound that is near a critical region of the central nervous system, such as the spine. The therapeutic agent may be dispersed within the scaffold by any useful method, e.g., by adsorption and/or absorption. For example, the therapeutic agent may be dissolved in a solvent (e.g., DMSO) and added to the scaffolding. In another embodiment, the therapeutic agent is mixed with a carrier polymer (e.g., polylactic-glycolic acid microparticles, agarose, a poly(ester urethane) urea elastomer (PEUU) or a poly(ether ester urethane) urea elastomer (PEEUU)), which is subsequently dispersed within the scaffold. By blending the therapeutic agent with a carrier polymer or elastomeric polymer, the rate of release of the therapeutic agent may be controlled by the rate of polymer degradation and/or by release from the polymer by diffusion or otherwise. Likewise, a therapeutic agent may be provided in any dissolvable matrix for extended release, as are known in the pharmaceutical arts, including sugar or polysaccharide matrices.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors $\alpha$ and $\beta$ (TGF-$\alpha$ and TGF-$\beta$), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In further embodiments, the scaffold can be cross-linked to a device, such as an implant, to increase bioacceptability of the implant and/or to increase attachment of the device. Methods of cross-linking of the scaffold to other surfaces are well-known. As an example, one or more surfaces of a hip joint restructuring device, such as a portion of a replacement femoral ball joint that comes in contact with a patient's femur, may be cross-linked to the scaffolding.

In its commercial use, the scaffold described herein can be distributed in dried or hydrated form. In one embodiment, the scaffold is distributed in gel (e.g., hydrated or hydrogel) form. In another embodiment, the scaffold is distributed in dried form. For example, dried powder can be reconstituted by an end-user, or intermediary. It may be preferable to distribute the scaffold as a kit comprising dried scaffold and a suitable solution for rehydration of the sample. The scaffold may be distributed as a powder, or as granules, depending on how finely the powder was comminuted during preparation.

In one embodiment, the scaffolding is distributed in a kit as a dry powder or granules in a container, along with a syringe that fits an opening on the container (that is, the container comprises a coupling for a syringe, such as a Luer lock, or a piercable closure, or the like). The kit optionally comprises a hydrating solution, that is any suitable (e.g., sterile) aqueous solvent, such as water or saline), and which can be contained within the syringe during distribution. In use, the end-user injects the aqueous solvent into the container by either fitting the syringe onto the container or piercing the pierceable closure and then hydrates the scaffold and fills the syringe with the hydrated scaffold for injection as a means for implantation. One or more therapeutic agents also may be dispersed either in the dry scaffolding or the solution used to rehydrate the scaffolding. Optionally, cells can be distributed throughout the powder when hydrated for suitable uses, such as in wound healing.

In another embodiment, a device is provided, as described above, comprising an implantable cover (generic for any three-dimensional container that contains the scaffold in a defined shape, such as cartilage- or breast-implant-shaped, and which can be implanted along with the scaffold) and the adipose-derived scaffolding dispersed within the cover. The implant may be distributed in dry form for hydration by an end-user, or it may be distributed in hydrated form.

EXAMPLE 1

Comparison of Three Methods for the Derivation of a Biologic Scaffold Composed of Adipose Tissue Extracellular Matrix The objective of the present study was to characterize the adipose ECM material resulting from three methods of decellularization in order to determine the most effective method for the derivation of an adipose tissue ECM scaffold which was largely free of potentially immunogenic cellular content while retaining tissue-specific structural and functional components as well as the ability to support the growth and adipogenic differentiation of adipose derived stem cells (ADSC). The results show that each of the decellularization methods produced an adipose ECM scaffold that was distinct from both a structural and biochemical perspective, highlighting the importance of the decellularization protocol used to produce adipose ECM scaffolds. Further, the results suggest that the adipose ECM scaffolds produced using the methods described herein are capable of supporting the maintenance adipogenic differentiation of ADSCs and may represent effective substrates for use in tissue engineering and regenerative medicine approaches to soft tissue reconstruction.

The objective of the present study was to characterize the adipose ECM material resulting from three distinct methods of decellularization in order to determine the most effective method for the derivation of an adipose tissue ECM scaffold which was largely free of potentially immunogenic cellular content, in this case DNA and cytoplasmic lipid, while retaining adipose tissue-specific structural and functional components. The efficacy of removal of cellular content, the effect upon ultrastructure, surface composition, maintenance of several ECM components and growth factors, and the ability of the resulting material to support the in vitro growth and differentiation of adipose derived stem cells (ADSCs) towards an adipogenic lineage were investigated for each method.

Materials and Methods
Preparation of Adipose Tissue ECM

Porcine adipose tissue was obtained from market weight pigs (approximately 240-260 lbs.) at a local abattoir. Tissue was frozen at −80° C. prior to slicing into 3 mm sheets using a rotary blade. Adipose tissues were then treated with one of three decellularization methods as described below. Table 1 contains a summary of each decellularization method.

TABLE 1

Steps for each decellularization method.

| Step # | Method A | Method B | Method C |
|---|---|---|---|
| 1 | Thaw tissue | Thaw tissue | Thaw tissue |
| 2 | Rinse in distilled deionized water (ddH$_2$O) | 3 mg/g dry weight collagenases digestion | 3 mg/g dry weight collagenases digestion |
| 3 | Mechanical massaging | 0.02% trypsin, 0.05% EDTA, 10 U/mL deoxyribonuclease | 0.1% NP40 |
| 4 | 0.02% trypsin, 0.05% EDTA | 10 U/mL lipase | 4% sodium deoxycholate |
| 5 | Rinse in ddH$_2$O | Rinse in PBS and ddH$_2$O | 1% SDS |
| 6 | Mechanical massaging | Lyophilization | 0.9% NaCl in Tris-HCl w/ protease inhibitors |
| 7 | 3% Triton X-100 | | Rinse in PBS and ddH$_2$O |
| 8 | Rinse in ddH$_2$O | | Lyophilization |
| 9 | 4% sodium deoxycholate | | |
| 10 | Rinse in ddH$_2$O | | |
| 11 | 4% ethanol, 0.1% peracetic acid | | |
| 12 | Rinse in PBS and ddH$_2$O | | |
| 13 | Lyophilization | | |
| 14 | 100% n-propanol | | |
| 15 | Rinse in ddH$_2$O | | |
| 16 | Lyophilization | | |

Method A:

Frozen adipose tissue was thawed in water and manually massaged to hasten the lysis of cells. Tissue was placed into a flask containing 0.02% trypsin/0.05% EDTA solution and incubated at 37° C. for one hour then rinsed briefly in distilled deionized water (ddH$_2$O) and manually massaged again. Tissue was then placed into a flask containing 3% Triton X-100 and placed on an orbital shaker for 1 hour at room temperature. Following a brief water rinse, tissue was placed into a 4% deoxycholic acid solution and again placed on an orbital shaker for 1 hour at room temperature. Tissue was rinsed three times in water and stored at 4° C. overnight. The tissue was then subjected to a 4% ethanol and 0.1% peracetic acid solution on an orbital shaker for 2 hours at followed by two phosphate buffered saline (PBS, pH 7.4) and two water washes of 15 minutes each at room temperature. The resulting material was then washed in 100% n-propanol for one hour on an orbital shaker at room temperature and washed in four changes of ddH$_2$O for one hour to remove the n-propanol prior to lyophilization.

Method B:

Frozen adipose tissue was thawed and then subjected to a previously described decellularization method (U.S. Pat. No. 6,777,231). Briefly, sheets of adipose tissue were subjected to collagenase digestion (3 mg/g starting tissue weight) for one hour at 37° C. on a shaker. The remaining tissue was then placed into a flask containing 0.02% trypsin/0.05% EDTA and 10 U/mL deoxyribonuclease in water for one hour followed by 10 U/mL lipase for one hour. The remaining material was then rinsed in PBS and then water three times each for 15 minutes per wash on an orbital shaker at room temperature and lyophilized.

Method C:

Frozen adipose tissue was thawed and then subjected to a previously described decellularization method (U.S. Pat. No. 6,777,231). Briefly, sheets of adipose tissue were thawed and collagenase digestion (3 mg/g starting tissue weight) was performedfor one hour at 37° C. on a shaker.

The remaining tissue was then incubated in a flask containing 0.05% EDTA in water for one hour followed by 0.1% nonyl phenoxylpolyethoxylethanol (NP40) for 1 hour, 4% sodium deoxycholate for 1 hour, 1% SDS for 1 hour, and 0.9% NaCl in TRIS-HCl containing protease inhibitors (1 mM phenylmethylsulfonyl fluoride, 5 mM benzamidine, and 10 mM N-ethylmaleimide) for one hour on an orbital shaker at room temperature. The remaining material was then rinsed in PBS and water three times each for 15 minutes and lyophilized.

Characterization and Confirmation of Decellularization

Samples of materials resulting from each decellularization method were fixed in formalin and embedded in paraffin or frozen in optimal cutting temperature solution then sectioned at 6 μm and affixed to glass slides. Oil red O staining was used to visualize the lipid content remaining within each material. Decellularization of the scaffold materials was assessed by hematoxylin and eosin staining (H&E), immunofluorescent labeling with 4', 6-diamidino-2-phenylindole (DAPI), quantification of the presence and length of any remaining DNA fragments by agarose gel electrophoresis, and quantification of DNA content by PicoGreen assay. All staining and assays were performed per manufacturer protocol or as previously described (Gilbert T W, et al. Quantification of DNA in biologic scaffold materials. J Surg Res. 152:135-9. 2009). Materials were considered to be fully decellularized if (1) no intact nuclei were visible in samples stained with H&E or sections labeled with DAPI, (2) no DNA fragments with a length greater than 200 bp were observed, and (3) the total DNA content was less than 50 ng of double stranded DNA/mg of scaffold dry weight. These values were selected based upon previous work which assessed levels of DNA remaining within commercially available ECM products.

Scanning Electron Microscopy

The ultrastructure of each sample was examined by scanning electron microscopy (SEM). Samples were fixed in cold 2.5% (v/v) glutaraldehyde in PBS for at least 24 hours, followed by three washes in PBS. Lipid fixation was performed in 1% (w/v) osmium tetroxide (Electron Microscopy Sciences) for 1 hour followed by three washes in PBS. Fixed samples were then dehydrated using a graded series of ethanol-water soltions (30-100%) followed by 15 minutes in hexamethyldisylizane and subsequent air-drying. The dried samples were mounted onto aluminum stubs and sputter coated with a 3.5 nm layer of gold/palladium alloy using a Sputter Coater 108 Auto (Cressington Scientific Instruments, Watford, England, UK). Images were taken with a scanning electron microscope (JEOL JSM6330f) at 1000× and 5000× magnification with an accelerating voltage of 3 kV.

Time-of-Flight Secondary Ion Mass Spectroscopy

Time-of-flight secondary ion mass spectroscopy (ToF-SIMS) analysis was performed at the National ESCA and Surface Analysis Center for Biomedical Problems (NESAC/BIO, University of Washington, Seattle, Wash.) using an IONTOF TOF.SIMS 5 instrument (IONTOF, Munster, Germany) as previously described (Brown B N, et al. Surface characterization of extracellular matrix scaffolds. Biomaterials. 31:428-37). Briefly, lyophilized samples were affixed to an aluminum stage, loaded into the ToF-SIMS instrument and a pumped to approximately $1 \times 10^{-9}$ mbar. The samples were then bombarded using a 25 keV $Bi_3^+$ primary ion source. The resulting secondary ions were collected and analyzed using a reflectron time-of-flight mass analyzer. At least five areas of approximately 0.01 mm$^2$ were selected at random from each sample for analysis and each sample was analyzed in duplicate, generating a total of at least 10 spectra per sample. Both positive and negative spectra were acquired from each sample; however, only the positive spectra are presented here as few characteristic and relevant peaks and were found in the negative spectra.

Immunolabeling of Extracellular Matrix Molecules

Formalin fixed samples were embedded in paraffin for histologic sectioning. Samples were cut into 6 μm sections and affixed to glass slides. Prior to immunolabeling the slides were dewaxed by immersion in xylenes followed by a graded series of ethanol-water solutions (100%-70%). Immunolabeling was performed with antibodies specific to a variety of ECM components (Table 2). Briefly, following dewaxing, all slides were subjected to antigen retrieval by immersion in 95-100° C. in citric acid solution (10 mM, pH 6.0) followed by rinsing in a 1× Tris buffered saline/Tween-20 solution (0.1% Tween 20 v/v, pH 7.4). Samples were then washed in PBS and treated with a pepsin digestion (0.05% pepsin w/v in 10 mM HCl) solution for further antigen retrieval. Samples were blocked against non-specific binding using a solution consisting of 2% serum, 1% BSA, 0.1% Tween-20, and 0.1% Triton X-100 in PBS for 30 minutes at room temperature. Primary antibodies were diluted in the blocking solution (dilutions of all antibodies are listed in Table 2) and applied to sections overnight at 4° C. Samples were washed in PBS and appropriate fluorescently labeled secondary antibodies (AlexaFluor 488) were applied for 30 minutes at room temperature. All secondary antibodies were diluted 1:250 in the blocking solution. Slides were washed in PBS and coverslipped in aqueous mounting media prior to visualization under a fluorescent microscope (Nikon e600).

TABLE 1

| Antibody | Dilution | Company |
|---|---|---|
| Mouse Anti-Collagen I | 1:2000 | Sigma C2456 |
| Mouse Anti-Collagen III | 1:2000 | Sigma C7805 |
| Rabbit Anti-Collagen IV | 1:200 | Biodesign T59106R |
| Collagen VII | 1:10 | Abcam |
| Rabbit Anti-Laminin | 1:200 | Sigma L9393 |

Growth Factor Assay

Lyophilized samples were minced into pieces of approximately 3 mm×3 mm. Six hundred mg of minced ECM was then suspended in 9 mL of urea-heparin extraction buffer (2 M urea and 5 mg/mL heparin in 50 mM tris with protease inhibitors: 1mM phenylmethylsulfonyl fluoride, 5 mM benzamidine, and 10 mM N-ethylmaleimide) at pH 7.4. The extraction mixture was rocked at 4° C. for 20 to 24 hours and then centrifuged at 3000 g for 30 minutes to separate remaining solid material from extracted supernatant. Supernatants were collected and 9 mL of freshly prepared urea-heparin extraction buffer was added to each pellet. Pellets with extraction buffer were re-extracted by rocking at 4° C. for 20 to 24 hours followed by centrifugation at 3000 g for 30 minutes, and supernatants were again collected. Supernatants from first and second extractions were dialyzed at 4° C. against ddH$_2$O (total of three changes of dialysis water, 80 to 100 volumes per change) in Slide-A-Lyzer Dialysis Cassettes with a 3500 molecular weight cut off (Pierce Protein Research Products, Thermo-Fisher Scientific Rockford, Ill.). The concentration of total protein in each extract was determined by the Bicinchoninic Acid Protein Assay (Pierce) following the manufacturer's protocol, and extracts were stored frozen in aliquots until time of assay.

Concentrations of basic fibroblast growth factor (bFGF) and vascular endothelial growth factor (VEGF) within urea-heparin extracts of adipose ECM samples were measured with the Quantikine Human bFGF Immunoassay (R&D Systems, Minneapolis, Minn.) and the Quantikine Human VEGF Immunoassay (R&D Systems). Concentrations of transforming growth factor beta 1 (TGF-β1) within urea-heparin extracts were measured with the Quantikine Mouse/Rat/Porcine/Canine TGF-β1 Immunoassay (R&D Systems). Manufacturer's instructions were followed for all three growth factor assays. Each assay for bFGF and VEGF was performed in duplicate; each assay for TGF-β1 was performed in triplicate. Each growth factor assay was performed two times. A one-way analysis of variance with Tukey's post-hoc test was used to determine statistical significance.

Glycosaminoglycan Assay

GAG concentrations were measured using the Blyscan Sulfated Glycosaminoglycan Assay Kit (Biocolor Ltd). Samples were prepared by digestion of 50 mg/ml dry weight ECM in 0.1 mg/ml proteinase K in 10 mM Tris, pH 8.0, 50 mM NaCl, and 1 mM EDTA for 24 h at 50° C. Digested samples were then assayed following the manufacturer's protocol. Each assay was performed in duplicate. A one-way analysis of variance with Tukey's post-hoc test was used to determine statistical significance.

Adipose Derived Stem Cell Culture on Adipose ECM Materials

Derivation of Adipose Derived Stem Cells

Human adipose tissue was digested in a collagenase solution (0.1% type 2 collagenase and 3.5% bovine serum albumin in 1× Hanks solution). Following digestion of the adipose tissue, the resulting solution was filtered through gauze to remove undigested material. The filtered solution was then centrifuged at 10,000 rpm for 10 minutes at 20° C. Supernatant was removed and the pellet was resuspended in 10 mL of erythrocyte lysis buffer (154 mM $NH_4Cl$, 10 mM $KHCO_3$, 1 mM EDTA in water, sterile filtered). Resuspended pellets were vortexed to lyse red blood cells and debris, and then recentrifuged at 10,000 rpm for 10 minutes at 20° C. The supernatant was then removed and the pellet resuspended in 10 mL of ADSC culture medium (1:1 DMEM and DMEM F12, 10% fetal bovine serum, 0.1 mM penicillin, 0.06 mM streptomycin, 0.1 mM dexamethasone, and 10 mg/L gentamycin sulfate). Cells were expanded in culture for no more than 2 passages prior to being seeded onto ECM scaffolds.

Adipose Derived Stem Cell Viability on Adipose ECM Scaffolds

ADSC culture medium was added to each adipose ECM and incubated in a 37° C., $CO_2$ regulated incubator for 24 hrs prior to cell seeding. $6 \times 10^6$ ADSCs were seeded onto each of the adipose ECM materials and were maintained in ADSC medium. Cell culture was stopped at 24 hrs and 72 hrs post-seeding and live/dead staining was performed.

For live/dead staining, the cell seeded adipose ECM scaffolds were washed twice with PBS and then incubated for 10 minutes in a 1:1 mixture of 0.01 mg/ml propidium-iodide (PI, Sigma Aldrich, Mo.) and 5 ug/ml fluorescein diacetate (FDA, Sigma Aldrich). Seeded materials were then imaged using a confocal microscope (Olympus Fluoview 1000MP, Olympus America Inc., Center Valley, Pa.). Images were taken at sequential planes and flattened into one single plane using Metamorph software (Molecular Devices, Sunnyvale, Calif.). Five different representative low power fields were taken from each sample and signal densities from PI and FDA measured with Metamorph software and used to determine the percentage of live and dead cells within the materials.

In Vitro Adipogenic Differentiation of Adipose Derived Stem Cells on Adipose ECM Scaffolds ADSCs ($3 \times 10^6$) suspended in ADSC culture medium were seeded onto the surface of each adipose ECM material and allowed to attach to the surface for 24 hrs. ADSC medium was then replaced with adipogenic medium (Zen-bio Inc., Research Triangle Park, N.C.) for 7 days in order to induce differentiation of the ADSCs towards an adipogenic lineage followed by adipogenic maintenance medium (Zen-bio Inc.) for another 7 days in order to test the ability of the ECM scaffold materials to support the maintenance of an adipogenic phenotype. Following the 15 day culture period, the cell seeded adipose ECM scaffolds were washed twice with PBS prior to staining with 1.5% v/v Adipo-Red (Lonza, Walkersville, Md.). Labeled samples were imaged using a confocal microscope (Olympus Fluoview 1000MP, Olympus America Inc.).

Results

Preparation of Adipose Tissue ECM

Figure 2:
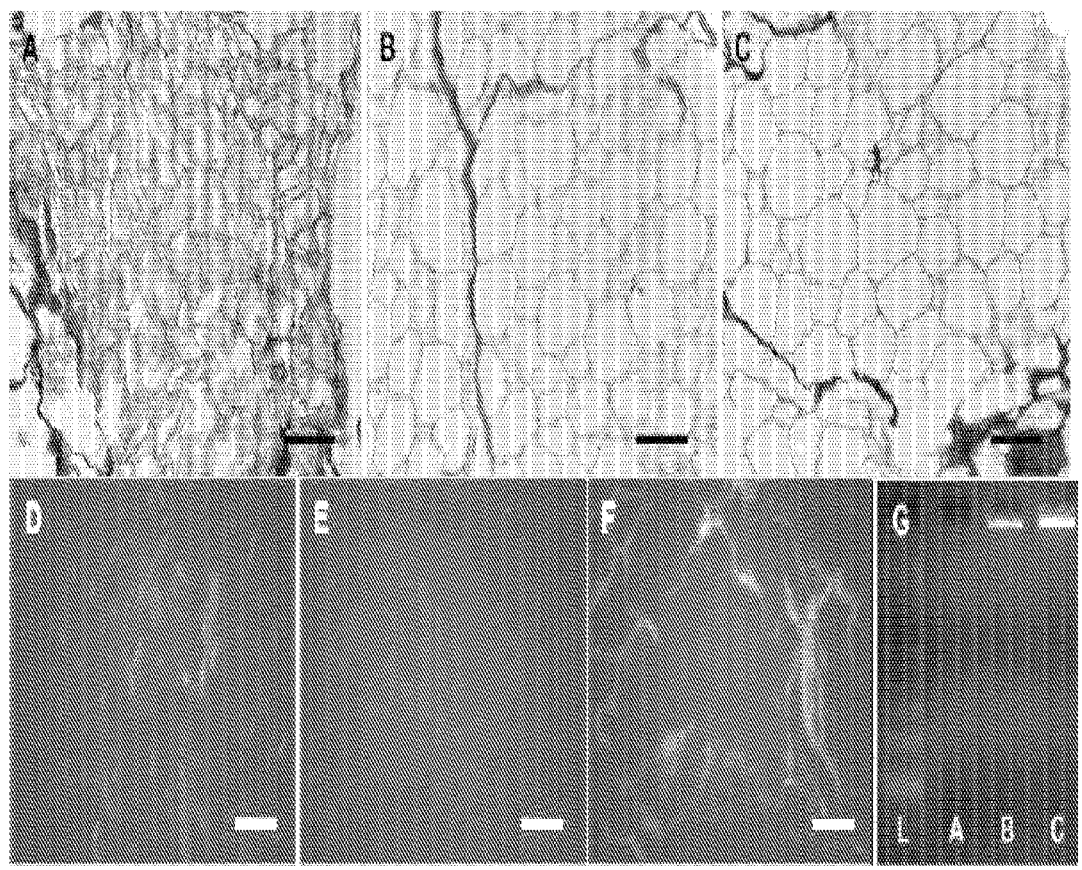
FIG. 2. Hematoxylin and eosin staining (A-C, 20× magnification), DAPI labeling (D-F, 20× magnification), and results of agarose gel electrophoresis of DNA isolated from each scaffold type (G). Scale bar=100 µm. Lane 1=DNA ladder, Lane 2=Method A, Lane 3=Method B, Lane 4=Method C.

The adipose ECM produced using Method A yielded a dry, white, fibrous material, while Methods B and C both produced white materials with a wet, shiny surface appearance indicative of high lipid content (FIG. 1A-C). Staining with oil red O showed that there was little to no lipid in samples produced using Method A, however lipid was shown to be present throughout samples produced using both Method B and C (FIG. 1D-F). All materials were found to be durable and elastic during handling while dry and following rehydration. No intact nuclei were observed in tissue sections stained with H&E (FIG. 2A-C) or labeled with DAPI (FIG. 2D-F) for any of the three methods. Scaffolds produced using Method A did not appear to contain any DNA as shown by agarose gel electrophoresis (FIG. 2G). Scaffolds produced using Methods B and C were shown to contain DNA of high by length as shown by gel electrophoresis (FIG. 2F). No DNA was detected by PicoGreen assay for scaffolds produced using Methods A and B. Scaffolds produced using Method C contained 78.1 ng DNA/mg scaffold dry weight.

Ultrastructural Examination Using Scanning Electron Microscopy

Figure 3:
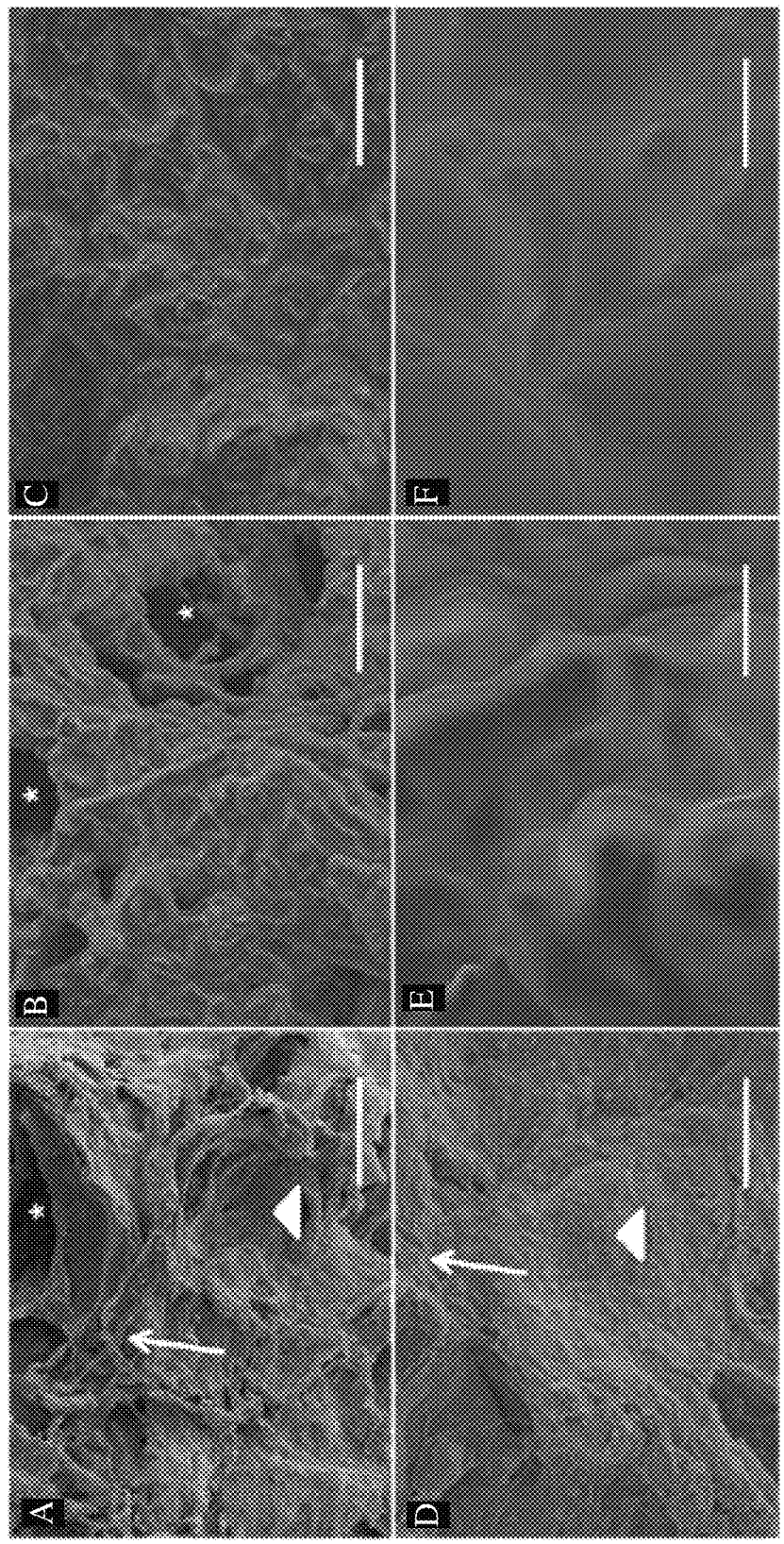
FIG. 3. Scanning electron micrographs of the surfaces of ECM materials decellularized with Method A (A, D), Method B (B, E), and C (C, F). Top panel (A-C)=1000× magnification, scale bar=25 µm. Bottom panel (D-F)=5000× magnification, scale bar=5 µm. Asterisks indicate vascular structures. Arrows indicate exposed fibrous extracellular matrix structures. Arrowheads represent exposed smooth basement membrane like surfaces. Small lipid droplets can be observed in A and D. Lipid surfaces indicated by smooth ultrastructure in B, C, E, and F are contiguous across the surface of the material.

Scanning electron micrographs were taken to examine the surface topography of the adipose ECM materials (FIG. 3). Both Methods B and C resulted in ECM with an uneven globular appearance at 1000× magnification indicative of high lipid content (FIG. 3A-C). Higher magnification (5000×, FIG. 3D-F) showed that these globules were smooth and contiguous with the rest of the ECM surface. In contrast, Method A resulted in a rough and uneven surface architecture indicative of collagenous ECM components at all magnifications examined. Smooth surfaces indicative of basement membrane and vascular structures were also visible throughout the scaffold material. Lipid droplets were observed in samples processed using Method A, but were less in size and number compared to those processed with Methods B and C. These results parallel those obtained using oil red O staining as described above.

Surface Composition Analysis Using Time-of-Flight Secondary Ion Mass Spectroscopy As shown by oil red O staining and SEM, adipose ECM samples prepared using Methods B and C contained large amounts of residual lipid and, therefore, could not be pumped to ultrahigh vacuum, thus precluding their analysis by ToF-SIMS. Therefore, the ToF-SIMS spectra obtained for adipose ECM derived using Method A were compared to those obtained previously for ECM materials derived from urinary bladder (UBM), small intestinal submucosa (SIS), and liver (LECM) in order to determine whether adipose tissue ECM possessed a distinct surface chemistry when compared to ECM scaffolds derived from other tissues (Brown B N, et al. Biomaterials. 31:428-37).

Figure 4:
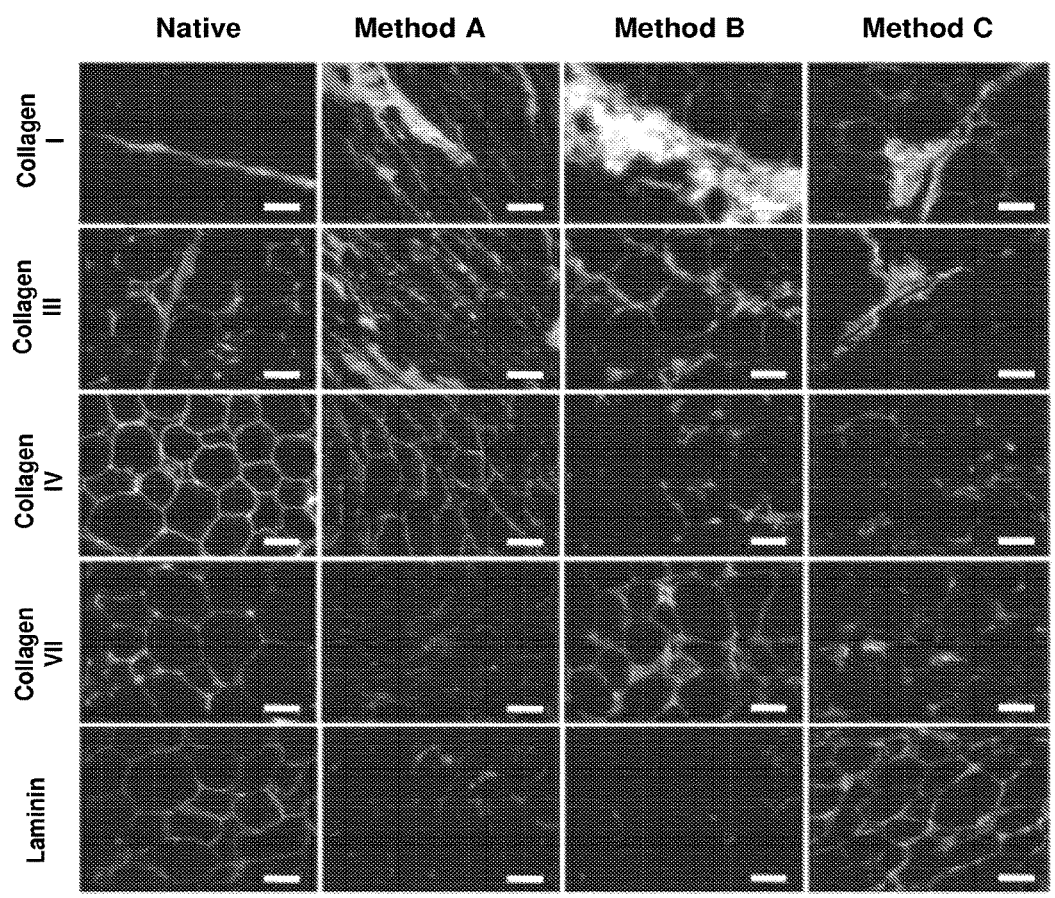
FIG. 4. Immunolabeling of collagen types I, III, IV, VII and laminin in samples decellularized with Methods A, B, and C. Immunolabeling of native adipose tissue is shown for comparison. All images 20× magnification. Scale bar =100 µm.

FIG. 4 shows a representative positive ion spectrum taken from the surface of decellularized adipose tissue prepared using Method A. A number of the prominent peaks found within the low mass region (m/z 0-150) labeled in FIG. 4 have been associated with the fragmentation patterns of amino acids in previous studies (Canavan H E, et al. Comparison of native extracellular matrix with adsorbed protein films using secondary ion mass spectrometry. Langmuir. 23:50-6. 2007 and Wagner M S, et al. Characterization of adsorbed protein films by time-of-flight secondary ion mass spectroscopy with principal component analysis. Langmuir. 17:4649-60. 2001). In FIGS. 4B-3E, peaks selected from a representative spectrum obtained from the luminal surface (dashed line) of urinary bladder ECM have been overlaid with a representative spectrum from the surface of the decellularized adipose tissue obtained using Method A (solid line). Low mass fragments observed in the spectra of UBM and adipose ECM were found to be overlapping, making them difficult to differentiate. FIGS. 4B and 3C are indicative of the difficulty inherent in comparing the low mass peaks observed in the present study to those obtained for UBM, SIS, and LECM scaffolds in previous studies. Despite these difficulties, FIG. 4D and FIG. 4E identify distinct fragments which were observed between the UBM and adipose ECM samples. For the peak at m/z 184, the fragment appears to exist primarily in the spectrum obtained from UBM while the peak at m/z 313 appears to exist primarily in the spectrum obtained from decellularized adipose tissue. Both peaks have been associated with lipid structures in previous studies (Wagner M S, et al. Langmuir. 17:4649-60. 2001; Magnusson Y. Application of multivariate analysis of ToF-SIMS Spectra for studying the effect of high glucose intake on aortic lipid profile. Applied Surface Science. 254:6580-5. 2008; McQuaw C M, et al. Lateral heterogeneity of dipalmitoylphosphatidylethanolamine-cholesterol Langmuir-Blodgett films investigated with imaging time-of-flight secondary ion mass spectrometry and atomic force microscopy. Langmuir. 21:807-13. 2005; and McQuaw C M, et al. Localization of sphingomyelin in cholesterol domains by imaging mass spectrometry. Langmuir. 23:5645-50. 200723-26).

To further quantify these differences, previously reported lipid peaks found within the spectra associated with the samples investigated in the present study were used to create two combined intensity ratios (Equations 1 and 2) (Brown B N, et al. Biomaterials. 31:428-37; Magnusson Y. Applied Surface Science. 254:6580-5. 2008; McQuaw C M, et al. Langmuir. 21:807-13. 2005; McQuaw C M, et al. Langmuir. 23:5645-50. 2007; and Baker M J, et al. Mass spectral imaging of glycophospholipids, cholesterol, and glycophorin a in model cell membranes. Langmuir. 24:11803-10. 2008). The first, $I_{MEM}$ (Equation 1), includes peaks that were chosen because of their existence in previous studies of cell membrane associated lipids and their prominence within the spectra of the UBM and SIS samples. The second, $I_{FAT}$ (Equation 2), includes predominantly higher mass peaks with the exception of the peak at m/z 605 which was prominent within the spectra obtained for Method A decellularized adipose ECM in the present study, but not has not yet been directly identified in the literature. These equations were chosen to demonstrate the most significant differences observed between the adipose ECM materials and other, previously examined ECM materials. Another method, such as principal components analysis, could have been used to show differences within the spectra obtained for each sample, however the results obtained would have been similar to those presented herein.

$$I_{MEM} = I_{104} + I_{166} + I_{184} + I_{224} + I_{369} + I_{385} \qquad \text{Equation 1}$$

$$I_{FAT} = I_{171} + I_{313} + I_{551} + I_{557} + I_{579} + I_{605} \qquad \text{Equation 2}$$

Figure 5A:
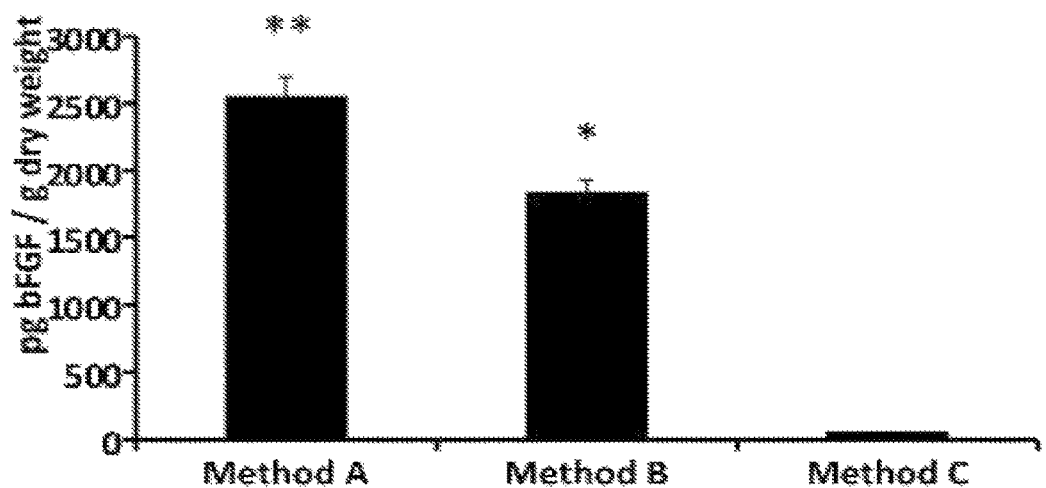
FIG. 5. Growth factor content of adipose ECM materials decellularized with Methods A, B, and C. Basic fibroblast growth factor content and vascular endothelial growth factor content are shown (A and B, respectively). Samples prepared using Methods A and B have higher bFGF and VEGF content than samples prepared with Method C (p<0.05). Samples prepared using Method A have a higher bFGF content than samples prepared using Method B (p<0.05). Results are shown as mean±standard error. ** indicates Method A samples have higher content than both Method B and Method C, p<0.05. * indicates statistical significance compared to Method C, p<0.05.
Figure 5B:
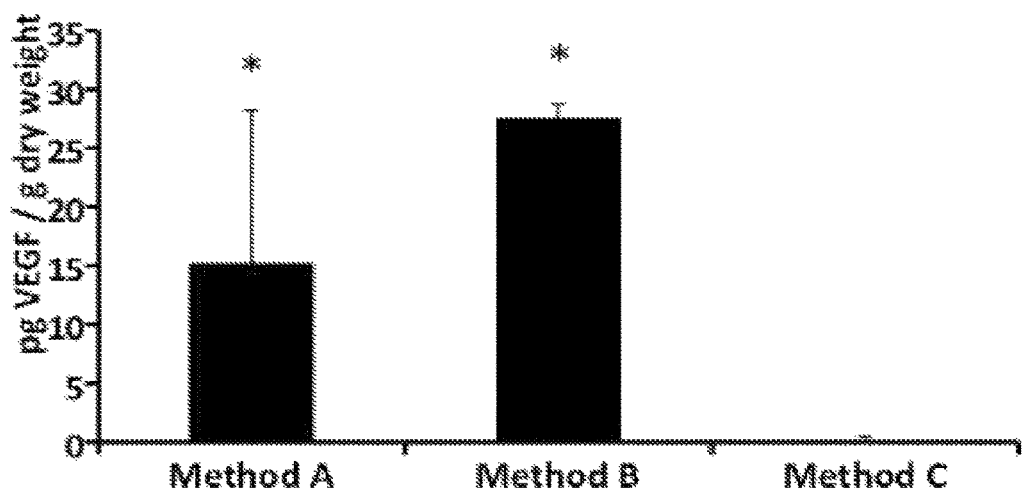

In FIG. 5 the combined normalized intensities have been plotted for the various surfaces examined in the present study. The peaks associated with cell membrane lipids ($I_{MEM}$) were seen prominently in the luminal and abluminal sides of both the UBM and SIS samples while contributing very little to the total ion intensity of the spectrum from the LECM or Method A adipose tissue ECM. Conversely, peaks associated with the Method A decellularized adipose tissue ($I_{FAT}$) contributed significantly to the total ion intensity of the spectrum from the decellularized adipose tissues while contributing very little to all other sample types. Lipid peaks from either set were not seen as prevalent in the LECM samples, suggesting that it possesses a surface chemistry which is distinct from all other samples investigated and contains smaller amounts of lipid content.

3.4 Immunolabeling of Extracellular Matrix Components

Figure 6:
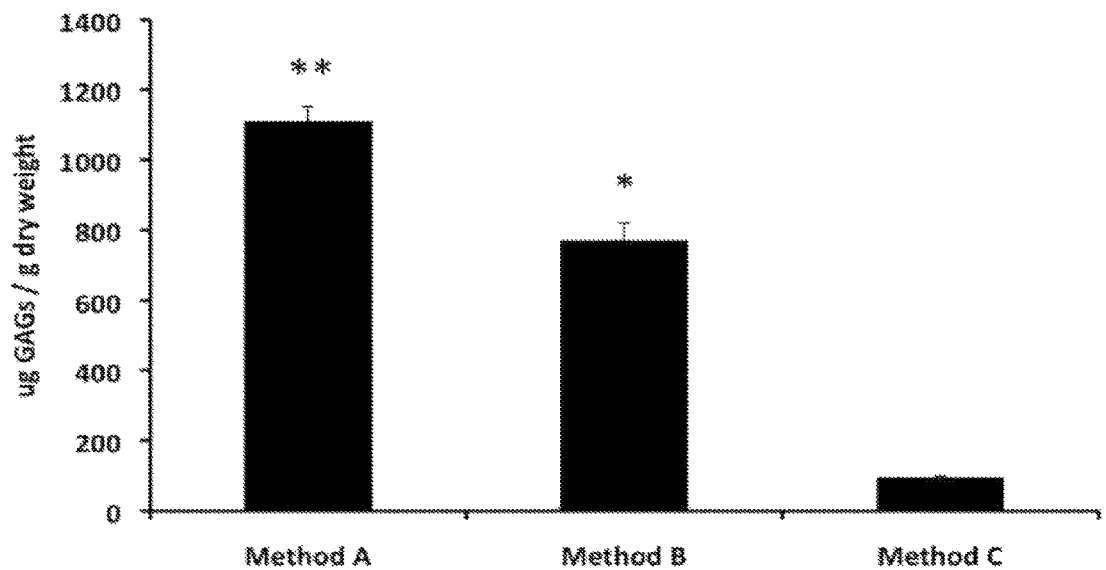
FIG. 6. Glycosaminoglycan content of ECM scaffolds decellularized using Methods A, B, and C. GAG content of scaffolds decellularized with Method A are higher than in samples prepared using Methods B or C (p<0.05), and levels in samples prepared with Method B are higher than in samples prepared using Method C. Results are shown as mean±standard error. ** indicates Method A samples have higher content than both Method B and Method C, p<0.05. * indicates statistical significance compared to Method C, p<0.05.

Immunolabeling showed that there were differences in the morphology and spatial distribution of a number of the ECM components investigated in this study, and that these differences were dependent on the decellularization protocol. FIG. 6 shows immunolabeling of the scaffolds resulting from each decellularization protocol. Immunolabeling of native porcine adipose tissue is also shown. Positive labeling for collagen I was found within the fibrous connective tissue present between adipocyte lobules in all of the samples investigated; however, the ultrastructure of the collagen I fibers was disrupted by all of the decellularization methods investigated resulting in a more loosely organized ultrastructure in the decellularized samples than was observed in the native tissue. Collagen III was found predominantly within the ECM surrounding adipocytes in native tissue and was also observed within the areas of fibrous connective tissue. Adipose tissue decellularized using Method A was positively labeled for collagen III primarily in the areas of the tissue formerly occupied by adipocytes, with similar results for tissues decellularized using Methods B and C. Collagen IV labeling was observed predominantly in the matrix associated with the adipocyte area and around blood vessels within native tissue. Positive labeling was observed in all decellularized samples. However, labeling for collagen type IV in samples decellularized using method A had a morphology which more similar to that observed in native tissue than was observed in samples decellularized using Methods B or C. Small amounts of positive labeling for collagen VII were observed in the native adipose tissue. This labeling was located predominantly within the matrix present between adipocytes and near blood vessels. Only small areas of collagen VII labeling were observed in the decellularized tissues and labeling for collagen type VII in tissues decellularized using Methods B and C was found predominantly in the areas of remaining blood vessel structures, with little labeling observed in the matrix associated with former adipocytes. Minimal labeling for collagen type VII was observed in samples decellularized with Method A. Laminin was observed in the same areas as collagen type IV labeling. Laminin was largely removed by all decellularization processes; however, tissues decellularized using C showed labeling which was similar to that observed for native tissue.

Growth Factor Content

Figure 7:
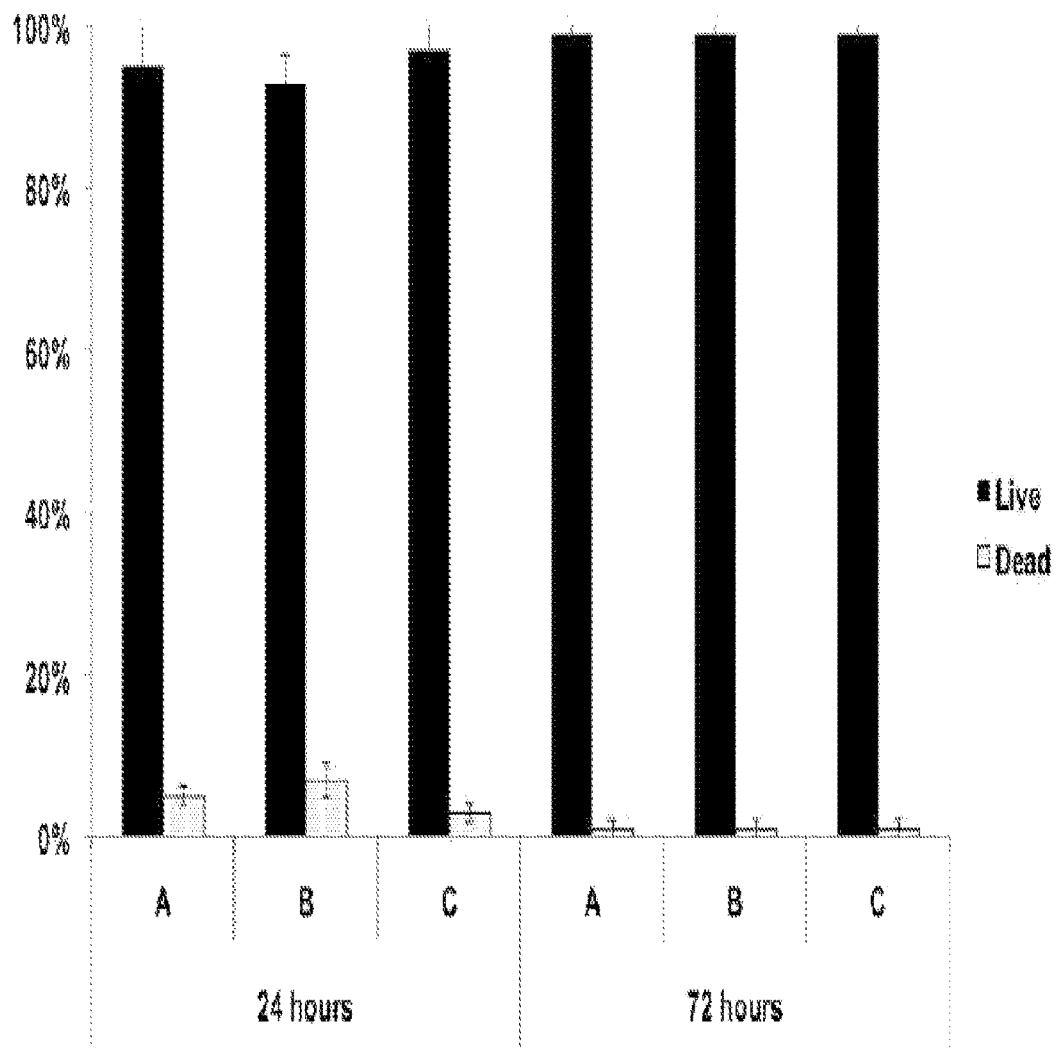
FIG. 7. Quantification of live/dead staining of adipose derived stem cells seeded onto ECM scaffolds decellularized using Methods A, B and C at 24 and 72 hours post seeding. No significant differences in cell viability were observed for any of the scaffold materials investigated. Percent live cells is represented by black bars. Percent dead cells is represented by white bars. Results are shown as mean±standard error.

The three methods used to prepare adipose ECM resulted in differences in growth factor content within the resulting materials (FIG. 7). bFGF was present at a 1.4-fold higher concentration in adipose ECM prepared using Method A (2551.8+/−148.1 pg per g dry weight) than in adipose ECM prepared using Method B (1840.5+/−92.3pg per g dry weight) ($p \leq 0.05$). 54.49+/−6.39 pg per g dry weight of bFGF was detected in adipose ECM prepared using Method C. VEGF was present at low levels in adipose ECM prepared by Methods A and B (15.2+/−13.0 pg per g dry weight and 27.6+/−1.2 pg per g dry weight, respectively), but these values were not found to be significantly different. VEGF was not detected in adipose ECM prepared by Method C. TGF-β1 was not detected in any of the porcine adipose ECM preparations.

Glycosaminoglycan Content

Figure 8:
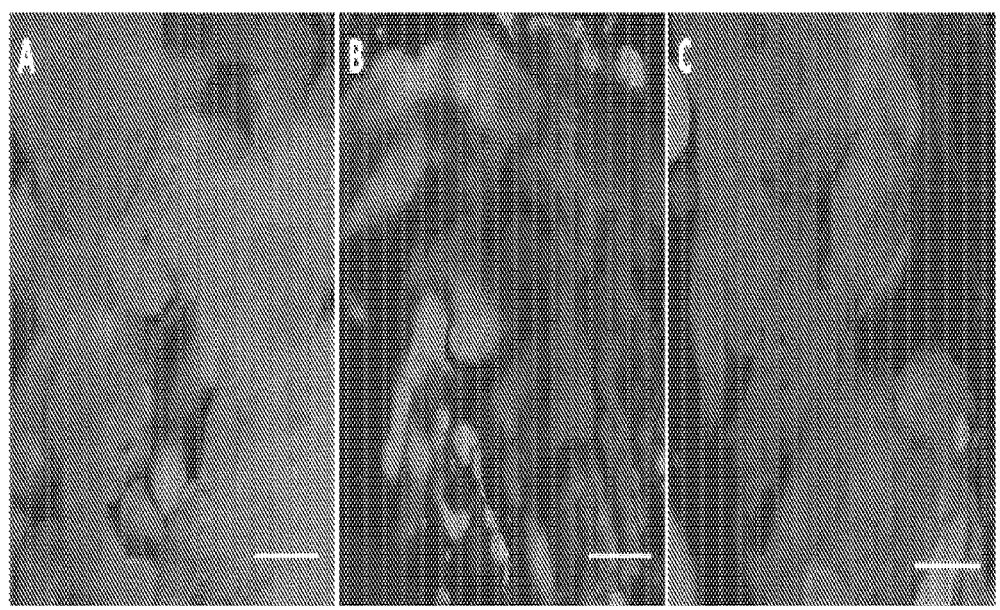
FIG. 8. Adipo-Red labeling of adipose derived stem cells seeded onto ECM scaffolds decellularized using Methods A, B and C, respectively. Scale bar=50 µm.

The three methods used to prepare adipose ECM resulted in differences in GAG content (FIG. 8). GAGs were present in ECM prepared using Methods A, B, and C at 1109.0+/−43.1 ug per g dry weight, 768.3+/−52.2 ug per g dry weight, and 95.2+/−4.3 ug per g dry weight, respectively. Adipose ECM prepared using method A had a 1.4-fold higher GAG content than the adipose ECM prepared using Method B ($p \leq 0.05$) and an 11.6-fold higher GAG content than porcine adipose ECM produced using Method C ($p \leq 0.05$). The GAG content of adipose ECM prepared by Method B was 8.1-fold higher than porcine adipose ECM prepared by Method C ($p \leq 0.05$).

Adipose Derived Stem Cell Culture

Figure 9A:
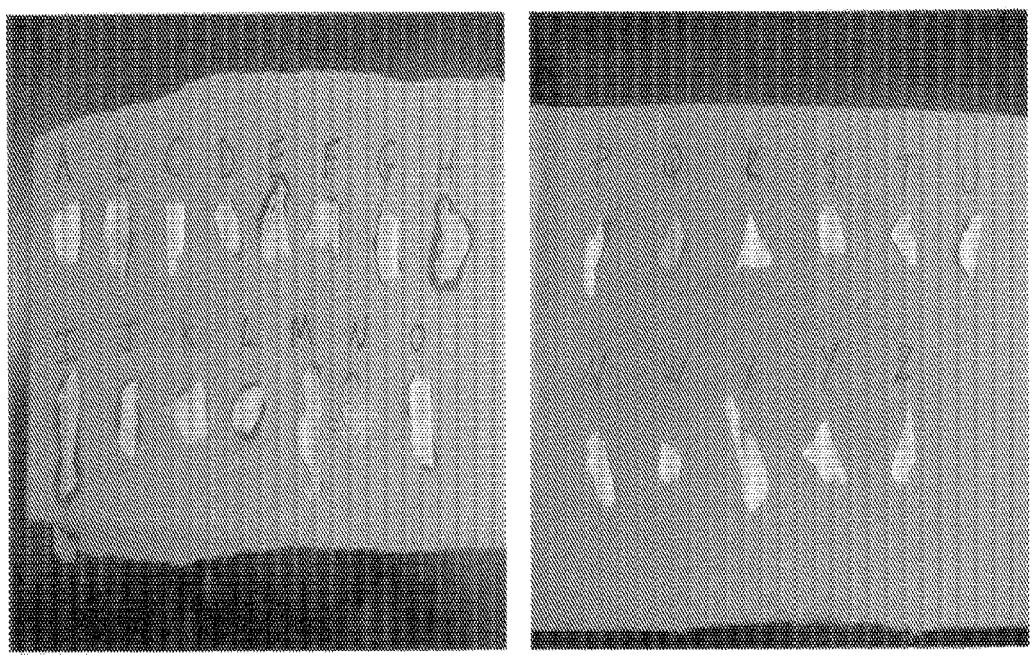
FIGS. 9A and 9B are photographs of decellularized adipose tissue prepared as indicated in Example 2.

ADSCs were seeded onto adipose ECM scaffolds and cultured in ADSC medium for 24 hrs and 72 hrs and then subjected to the live/dead assay described above to check ADSC viability. As shown in FIG. 9, approximately 95% of ADSCs seeded onto adipose ECM scaffolds and cultured in ADSC culture medium were viable at 24 hrs after seeding and cell viability was 99% at 72 hours post-seeding regardless of preparation method. There were no significant differences in cell survival among the three different porcine adipose ECM used.

Figure 10:
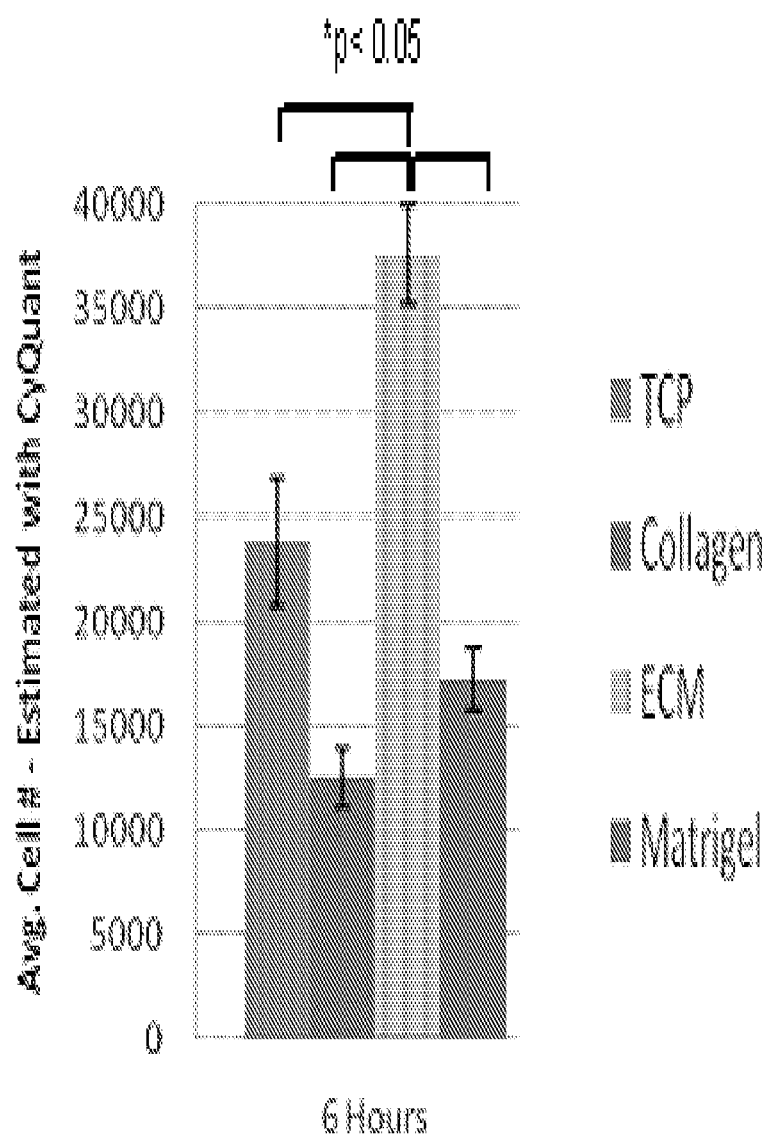
FIG. 10. Adherence of adipose stem cells to Fat ECM coated culture plates, left to right in graph (original in color) TCP, Collagen, ECM and Matrigel.

ADSCs were allowed to attach to the surface of each adipose ECM in ADSC medium for 24 hrs prior to culture in adipogenic medium for 7 days followed by adipogenic maintenance medium for another 7 days. Cell seeded scaffolds were then subjected to Adipo-Red labeling. As shown in FIG. 10, ADSCs seeded onto the surface of the three different types of porcine adipose ECM and cultured in adipocyte differentiation medium differentiated and maintained an adipocyte phenotype under in vitro conditions as evidenced by positive labeling using Adipo-Red, suggesting that all three types of porcine adipose ECM were able to support the in vitro growth and differentiation of ADSCs along an adipocyte lineage (FIG. 10).

DISCUSSION

Adipose ECM materials resulting from three decellularization protocols were investigated for the effectiveness of removal of cellular content, ultrastructure, surface composition, ECM component molecule content and distribution, and the ability to support the growth and adipogenic differentiation of ADSCs. Results show that each of the three decellularization methods investigated resulted in set of scaffold characteristics that was distinct from both a structural and biochemical perspective. While these findings are not surprising given the differences in the decellularization agents used in each method, the results of the present study demonstrate the importance of determining a decellularization protocol which is tailored to the tissue of interest; that is, a process which removes as much of the cellular material as possible with minimal adverse effects upon the biochemical composition, topographical ligand landscape, and biologic activity of the resulting scaffold material (Gilbert T W, et al. Biomaterials. 27:3675-83. 2006).

In the present study, Method A was shown to produce a scaffold material which had a surface topography which more resembled the fibrous and basement membrane ECM components of adipose tissue than did Method B or C, which possessed a topography which was indicative primarily of lipid structures at the surface of the scaffold material. Further examination of these materials using oil red O staining showed that Method A retained little to no lipid content following decellularization, while scaffolds processed using Methods B or C retained lipid content. Examination of the materials using immunolabeling showed that each decellularization method was associated with maintenance of a distinct set of ECM component molecules within the resultant scaffold. The spatial organization of these components was similar to that observed in native adipose tissue, suggesting that all of the decellularization processes maintained the structure of the native tissue to a large degree. Biochemical analysis showed that Method A retained more of the GAG and bFGF content than did Method B or C. Both Methods A and B were more efficient in maintenance of overall GAG and growth factor content than was seen with Method C, which resulted in significantly lower quantities of both GAG and growth factors within the resulting scaffold material. Despite the differences in structure and biochemical content observed in the present study, no differences were seen in the ability of the materials to support the in vitro growth, differentiation, and maintenance of ADSCs along an adipocyte lineage. However, the lack of differences in in vitro growth characteristics may have resulted from similarities in the adsorption of attachment proteins from the cell culture medium to each of the ECM materials. The ability of ADSCs to differentiate towards lineages other than adipogenic was not investigated in the current study.

Recent evidence suggests that tissue specific ECM may be more effective in supporting the maintenance of highly specific cell phenotypes. For example, a recent study showed that ECM scaffolds derived from the liver were more effective in supporting the maintenance of the phenotype of hepatic sinusoidal endothelial cells during in vitro culture than were ECM scaffolds composed of urinary bladder or small intestinal submucosa (6). The ability of certain ECM scaffolds to promote the maintenance of specific phenotypes and differentiation states may be related to differences in tissue specific architecture and molecular composition which have been observed in a number of recent studies; however, it is unclear whether the structural or the functional components of the material play a larger role in determining the outcome of cell-scaffold interactions (Badylak S F, et al. Extracellular matrix as a biological scaffold material: Structure and function. Acta Biomater. 5:1-13. 2009; Brown B, et al. The basement membrane component of biologic scaffolds derived from extracellular matrix. Tissue Eng. 12:519-26. 2006; and Brown B N, et al. Biomaterials. 31:428-37).

In the present study, the surface composition of ECM derived from porcine adipose tissue was compared to that of porcine UBM, SIS, and LECM using ToF-SIMS (Brown B N, et al. Biomaterials. 31:428-37). From the ToF-SIMS data shown in FIGS. 4 and 5, it can be seen that the adipose ECM produced using Method A has a distinct spectral signature when compared to scaffolds derived from UBM, SIS, and LECM. The prominence within the adipose ECM of the peaks in the higher mass region (above m/z 500) that are not prominent in UBM, SIS, or LECM scaffolds provides further insight into the surface characteristics of the decellularized adipose tissues. The existence of these high mass peaks may be indicative of a preserved set of macromolecules on the surface. While not investigated in the current study, this hypothetical retention of intact surface macromolecules could play a significant role in determining the outcome of interactions of adipose tissue specific cells with these surfaces, both in vitro and in vivo, due to the presentation of whole, intact molecular functional groups. The variation in surface molecular functionality could be integral in guiding tissue specific cellular responses that could be characterized in future studies and potentially related back to the surface differences observed in the present study.

Many studies have shown that ECM scaffolds are capable of supporting the growth of a variety of cell types in vitro as well as acting as templates for the functional reconstruction of a wide variety of tissues and organs in vivo. Although the mechanisms by which these materials support and promote a constructive remodeling process are only partially understood, it appears clear that rapid degradation of the scaffold material with concurrent release of both intact growth factors and newly generated bioactive matricryptic peptides as well as the provision of unique surface architectures are factors that play an important role. The ability to promote constructive remodeling in vivo has also been shown to be highly dependent on the methods used in preparing the scaffold material. For example, chemical crosslinking is often used to increase the mechanical strength of a scaffold material, to slow degradation, or to mask cellular epitope which may remain within the scaffold material following decellularization. While the rationale for using crosslinking in the production of ECM scaffold materials is understood, a number of studies which have compared non-crosslinked matrices to matrices which have been crosslinked using chemical methods have shown a less desirable tissue remodeling response when ECM scaffolds have been altered using chemical crosslinking. The exact reasons for the differences in tissue remodeling are not clear, but are likely related to the inability of the material to degrade and release bioactive components or through alteration of the bioactive ligands present on the surface of the scaffold material. Similarly, a recent study showed that the presence of a large amount of cellular content within an ECM scaffold led to a more inflammatory type host response following implantation and resulted in the formation of scar tissue within the site of remodeling (Brown B N, et al. Macrophage phenotype and remodeling outcomes in response to biologic scaffolds with and without a cellular component. Biomaterials. 30:1482-91. 2009). This response is in contrast to the constructive remodeling that was observed when the same material was effectively decellularized prior to implantation, again highlighting the importance of the methods of production in determining the tissue remodeling outcome associated with implantation of an ECM scaffold material.

The results of this study showed that Methods A and B resulted in efficient decellularization of adipose tissue, while Method C did not (78.1 ng DNA/mg dry weight). While the scaffolds resulting from each decellularization method examined in this study supported the growth and differentiation of ADSCs, there is concern that incomplete decellularization may lead to an adverse host response following implantation which will affect the downstream ability of the scaffold material to support constructive remodeling in vivo. Further, the effects of the excess cytoplasmic lipid observed within the biologic scaffolds produced using Methods B and C upon in vivo remodeling are unknown, but indicate that potentially immunogenic cellular contents may remain within the scaffold materials. Furthermore, the presence of excess lipid may adversely affect the ability to process scaffold materials into a configuration that is applicable for clinical approaches to tissue reconstruction.

CONCLUSION

Three methods for the preparation of decellularized adipose tissue were compared for effectiveness of decellularization, ability to maintain the structure and functional composition of ECM components, and the ability to support the growth and adipogenic differentiation of ADSCs. The results of the study showed that each decellularization method was associated with distinct structure and composition of the resulting material. Despite these differences, the ability to support the growth and adipogenic differentiation of ADSCs was unaffected. However, only Methods A and B achieved effective decellularization of the adipose tissue, and only Method A was shown to remove the majority of the lipid content of the adipose tissue. The presence of cellular remnants, including excess lipid, may affect the ability of an adipose ECM material to function as a template for constructive remodeling in vivo. This study shows the importance of the decellularization protocol and suggests that adipose ECM scaffolds derived using Method A as described herein may represent an effective substrate for use in tissue engineering and regenerative medicine approaches to soft tissue reconstruction.

EXAMPLE 2

The following compares various methods of preparing adipose tissue-derived cell growth scaffolds in their ability to effectively remove lipid residuals from the materials. A decellularized cell growth scaffold was prepared essentially as described according to method 1, up to the lyophilization step after disinfecting, depyrogenating and washing the tissue, represented by sample L of Table B, below. The lyophilized sample was divided and treated as indicated in Table B. Wet samples (A-K, O and P) were shaken for at least 1 hour at room temperature (RT, approximately 25° C.), and rolled under a mesh. Dry samples (Q-W) were tumbled at RT for 1 hour. An orbital shaker was used for agitation. Samples L-M were untreated, except that M and N were heated in an oven overnight for about 12 hours.

For the "Modified protocol", adipose tissue was sliced and gently massaged to lyse cells. 0.02% trypsin/0.05% EDTA solution was added and the tissue was incubated in a water bath for 1 hour at 37° C. The solution was strained and the tissue was rinsed under water and again massaged, if necessary. The tissue was shaken for 1 hour in a 3% Triton X-100 solution and massaged again, if necessary. The tissue was shaken for 1 hour in a 4% deoxycholic acid solution and thoroughly rinsed in water. Tissue was disinfected and dried essentially as described above.

TABLE B

| A | H$_2$0 | W* |
| B | Modified Protocol | W* |
| C | 100% EtOH | W* |

TABLE B-continued

| | | |
|---|---|---|
| D | 70% EtOH | W* |
| F | 50% Glycerol | W* |
| E | 50% Corn Oil | W* |
| G | 3% Triton X-100 | W* |
| H | 3% Triton X-200 | W* |
| I | 3% Tween 20 | W* |
| J | 3% SDS | W* |
| K | 3% Deoxycholate | W* |
| L | Lyophilized | D |
| M | Lyophilized then 70° | D |
| N | 60° then 80° | D |
| O | 3% NaOH | W* |
| P | 100% Isopropyl OH | W* |
| Q | Drierite | D** |
| R | Silica gel | D** |
| S | NaCl | D** |
| T | $CaCl_2$ | D** |
| U | Talc | D** |
| V | NaOH | D** |
| W | Alumina Oxide | D** |
| X | Blotting @ RT | D |
| Y | Blotting @ 37° | D |
| Z | Blotting @ 60° | D |

W Wet, agitated then rolled under mesh
D Dry
**With tumbling agitation

Figure 9B:
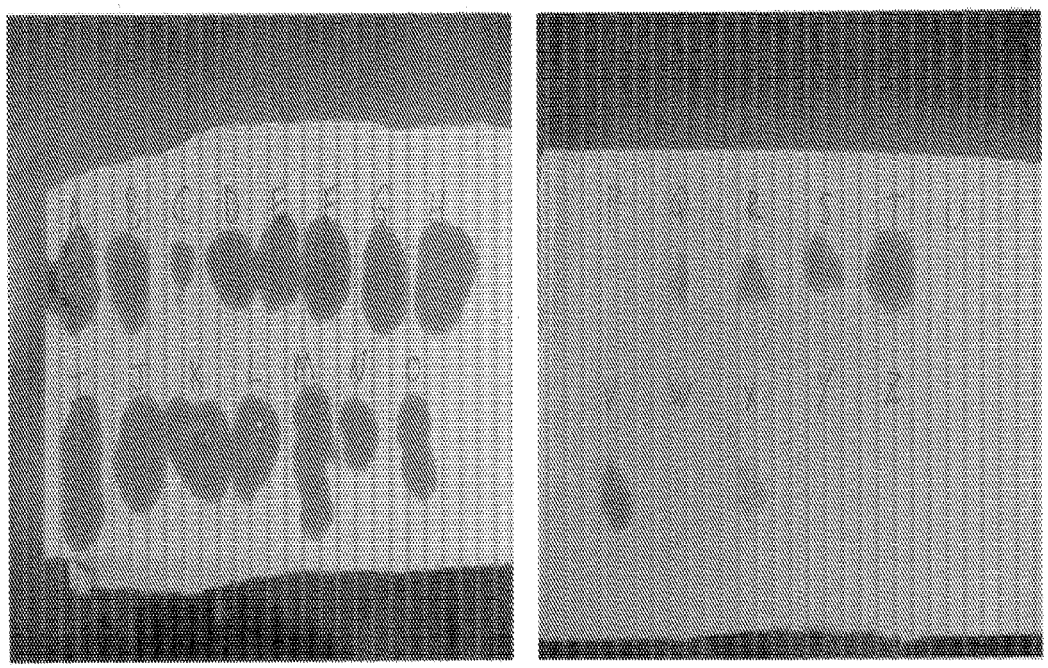

The samples were then blotted onto brown paper for several minutes (FIG. 9A), and then removed to visualize the amount of residual fats/oils, remaining (FIG. 9B).

EXAMPLE 3

In-Vitro and In-Vivo Experiments with Fat ECM

A. Six Hour Comparative In Vitro Adhesion/Proliferation Study on Surface of Fat ECM Gel
Aim: Assess the adherence and early proliferation of adipose derived stem cells on the surface of Fat ECM gel and compare with other culture surfaces.
Rationale: We hypothesized that the proteins within fat ECM gel will provide a favorable environment for the adherence and proliferation of adipose stem cells. This initial in-vitro experiment serves as the basis for pursuing additional studies described.
Methods: Human adipose tissue (obtained in accordance with all IRB regulations) was digested with a collagenase solution composed of type 2 collagenase (0.1%), with bovine serum albumin (3.5%) in 1× Hanks solution. This solution was then filtered through double layer gauze to remove unprocessed debris. The resulting filtered solution was centrifuged at 10,000 rpm for 10 minutes at 20° C. Supernatant was removed and the pellet was resuspended in 10 mL of erythrocyte lysis buffer. Erythrocyte lysis buffer is composed of 154 mM $NH_4Cl$, 10 mM $KHCO_3$, 1 mM ethylenediaminetetraacetic acid in water, and sterile filtered. Resuspended pellets were vortexed to lyse red blood cells and debris, and then recentrifuged at 10,000 rpm for 10 minutes at 20° C. The supernatant was then removed and the pellet resuspended in 10 mL of human regular media. Human regular media is composed of DMEM and DMEM F12 (Dulbecco modified eagle medium from Gibco) at a 1:1 ratio, 10% fetal bovine serum, 0.1 mM penicillin, 0.06 mM streptomycin, 0.1 mM dexamethasone, and gentamycin sulfate (10 mg/L). Cells were expanded in culture for no more than 2 passages before being used for this experiment. These cells are referred to as adipose stem cells (ASC's).

Figure 11:
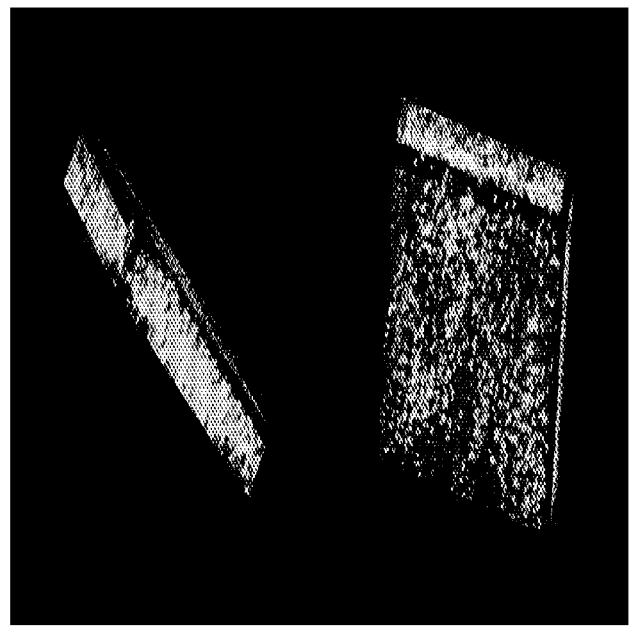
FIG. 11. Representative sample of cells encased within fat ECM showing nearly 100 percent cell viability at 2 hours, and greater than 90% viability at 24 hours (viable cells are green in original).

Culture plates were prepared (Tissue Culture Treated 24-well plates, BD, Franklin Lakes, N.J.) with thin-layer (200 µL) coatings of: Collagen Type 1 (3.89 mg/mL, 20:1 Collagen to NaOH, BD 354236), Matrigel™, and Fat Extracellular Matrix (6 mg/mL). Uncoated Tissue Culture Treated plates served as controls.
Wells were seeded with 30,000 ASC's, isolated by the method described above. After 6 hours, plates were washed with phosphate-buffered saline (PBS) to remove non-adherent cells. Cell number was determined by CyQUANT cell proliferation assay kit (Cat C35007, Molecular Probes, Eugene, Oreg.). Fluorescence was measured at 480 nm excitation and 520 nm emission (Tecan SpectraFluor, Tecan, Inc, Research Triangle Park, N.C.). A standard curve was created and cell number obtained.
Results: FIG. 10 shows cell number 6 hours after plating on the various surfaces. There is a statistically significant increase in the number of cells on the fat ECM coated wells.
Conclusion: Fat ECM is a highly favorable surface for the adherence of adipose derived stem cells.
B. Twenty-Four Hour Study of Survival of ASC's within Fat ECM Gel
Aim: With ASC adherence to fat ECM coated surface verified, we sought to determine if ASC's could survive encased within the Fat ECM gel.
Rationale: This study is a logical follow up to the surface adhesion experiment, and a useful precursor study for an animal trail of soft tissue engineering.
Methods: Fat ECM was admixed with 2 million ASCs (see methods above) per ml of fat ECM gel and poured into 12 well cultures plates to a thickness of 3-4 mm. Culture medium was applied over the solidified ECM, allowing nutrients to reach the cells only through diffusion. Cell viability was assessed measured "Live/Dead" assay (Propidium iodide solution (1:100) in PBS, and FDA (Fluorescein Diacetate) solution (1:1000) in PBS).
Results: FIG. 11 shows a representative sample with nearly 100 percent cell viability at 2 hours, and greater than 90% viability at 24 hours (Ratio of green to red signal).
Conclusion: Fat ECM can support the survival of ASC's encased completely within the gel.
C. Six Week In-Vivo Study of the Survival of ASC's within Fat ECM Gel in a Rodent Model
Aim: The aim of this study was to assess the ability of human ASC's to survive and form adipose tissue when seeded within fat ECM and implanted into a nude mouse model.
Rationale: A significant unmet need in clinical reconstructive surgery is the ability to regenerate soft tissue at the site of injury or cancer therapy. While major plastic surgery tissue flap procedures can help treat these deformities, there is significant donor site morbidity, extensive scarring, and a lack of precision in achieving the desired reconstructive outcome. Cell based therapies, especially involving autologous adipose stem cells, have the advantage of being minimally invasive but would only be effective when delivered with an adequate scaffold material. In this study, we hypothesized that the extracellular matrix derived from adipose tissue would be a favorable environment to support the growth of new fat tissue from ASC's.
Methods: Fat ECM was admixed with ASC's at a ratio of 1,000,000 cells per ml of gel. ASC's were expanded in culture prior to mixing with ECM, and were exposed to culture conditions with high concentrations of insulin and dexamethasone for 7 days just before the experiment. This "priming" of the ASC's facilitates adipogenic differentiation, but does not result in any visible lipid accumulation or other phenotypic changes. The seeded fat ECM was injected into the subcutaneous tissues of a nude mouse using a blunt cannula (n=3). This study was done in accordance with all animal care regulations. ECM without cells served as a control. Similar cell/scaffold preparations included Matrigel (n=3) fibrin glue (n=3), and commercial hyaluronic acid soft tissue fillers (n=3). Control groups of non-seeded scaffold were included for each material. Matrigel represents the current gold standard for an adipose tissue engineering scaffold. An additional positive control group of a lipoaspirate implant (n=3) was also used. Mice were sacrificed at 6 weeks. Specimens were excised, collected, fixed in 4% paraformaldehyde, and processed for H&E staining. Specimens were graded on a 4 point scale based on how closely the architecture resembled native adipose tissue.

Figure 12:
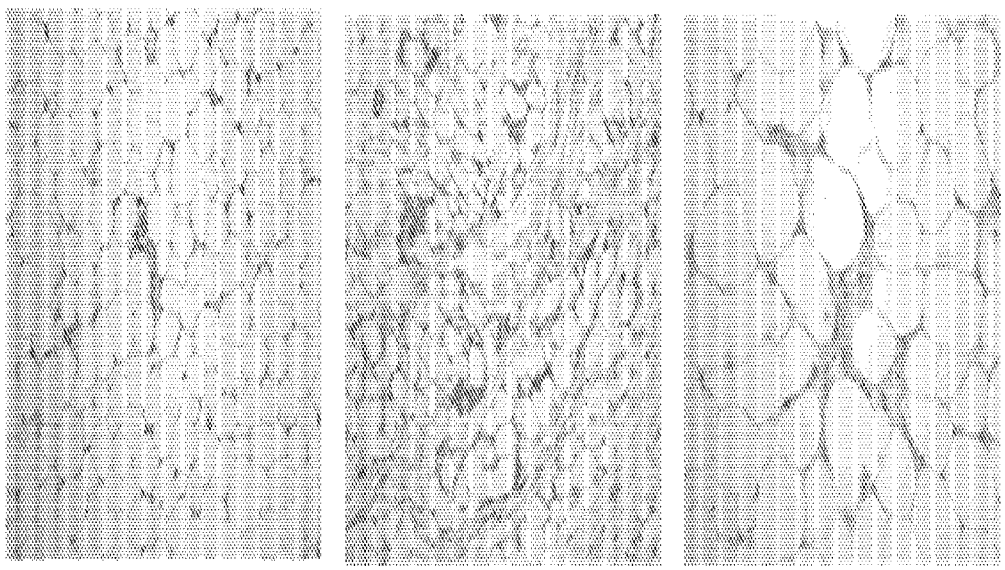
FIG. 12. Histologic appearance of Fat ECM gel seeded with ASC's and implanted for 6 weeks in a nude mouse. The Fat ECM produced adipose tissue resembling native fat.

Results: Fat ECM seeded with ASC's generated adipose tissue with the highest histologic score. This exceeded the ability of Matrigel, long held as the gold standard as an adipogenic scaffold. Table C shows the results of the various groups. All scaffold materials devoid of cells failed to produce any adipose tissue. FIG. 12 shows representative histology slides.

TABLE C

Histologic Analysis of implanted ECM in a nude mouse after 6 weeks

| Experimental Group | Histologic Findings after 6 weeks in-vivo | Histologic grading (0-4 scale) |
| --- | --- | --- |
| Lipoaspirate graft (positive control) | Mature adipose tissue, vascularized, with minimal scar formation | +4 |
| Fat ECM with Cells | Mature adipose tissue, vascularized, with minimal scar formation. Indistinguishable from control. | +4 |
| Matrigel with cells | Islands of adipose tissue with significant regions of scar | +2 |
| Fibrin glue with cells | Islands of adipose tissue with significant regions of scar | +2 |
| Commercial concentrated hyaluronic acid gel and cells | No adipose tissue detected | 0 |

Conclusion: Fat ECM is a favorable scaffold material for adipose tissue engineering. This material has great potential for clinical use.

As can be seen from the Examples, treatment with a propyl alcohol (e.g., isopropanol or n-propanol) is comparable or favorable to the more difficult and costly steps of dry blotting with tissue paper or treatment with talc aluminum oxide. The methods also do not require costly enzymatic digests, such as DNAse or lipase treatment, or protease inhibitors, as is described in the U.S. Pat. No. 6,777,231.

Having described this invention above, it will be understood to those of ordinary skill in the art that the same can be performed within a wide and equivalent range of conditions, formulations and other parameters without affecting the scope of the invention or any embodiment thereof.

We claim:

1. A method of preparing an adipose tissue-derived cell growth scaffold comprising, in order: digesting an adipose tissue sample with a proteinase and a chelating agent; washing the adipose tissue sample with an emulsifier; disinfecting the adipose tissue sample; depyrogenating the adipose tissue sample; drying the adipose tissue sample; and washing the adipose tissue sample with n-propanol, isopropanol or a mixture thereof.

2. The method of claim 1, wherein the method comprises the following steps, in order:
  a. rinsing an adipose tissue sample;
  b. mechanically massaging the adipose tissue sample;
  c. digesting the adipose tissue sample with a proteinase and a chelating agent;
  d. rinsing the adipose tissue sample;
  e. mechanically massaging the tissue sample;
  f. washing the adipose tissue sample with a surfactant while the adipose tissue sample is agitated;
  g. rinsing the adipose tissue sample;
  h. washing the adipose tissue sample with an emulsifier;
  i. rinsing the adipose tissue sample;
  j. disinfecting the adipose tissue sample;
  k. depyrogenating the adipose tissue sample;
  l. rinsing the adipose tissue sample;
  m. drying the adipose tissue sample;
  n. washing the dried adipose tissue sample in n-propanol, isopropanol or a mixture thereof;
  o. washing the adipose tissue sample in an aqueous solvent; and
  p. drying the adipose tissue sample.

3. The method of claim 2, in which in step m. the sample is dried by lyophilization.

4. The method of claim 2, in which step p. drying the sample comprises lyophilizing the sample.

5. The method of claim 2, further comprising step q. comminuting the sample to produce a powder.

6. The method of claim 5, wherein the powder has a maximum size of 250 µM.

7. The method of claim 1, in which the adipose tissue sample is washed with n-propanol.

8. The method of claim 1, in which the adipose tissue sample is washed with isopropanol.

9. The method of claim 1, further comprising after washing the adipose tissue sample with n-propanol, isopropanol or a mixture thereof, placing the adipose tissue sample in a covering prepared from one or more sheets of ECM material.

* * * * *